(12) United States Patent
Gharpure et al.

(10) Patent No.: US 12,347,573 B1
(45) Date of Patent: Jul. 1, 2025

(54) ARTIFICIAL INTELLIGENCE (AI) TO CREATE A PATIENT VISIT NOTE BASED ON A CONVERSATION BETWEEN A DOCTOR AND A PATIENT

(71) Applicant: SULLY.AI, Santa Clara, CA (US)

(72) Inventors: Chaitanya Gharpure, Santa Clara, CA (US); Ahmed Omar, Santa Clara, CA (US); Ahmed Nasser, Santa Clara, CA (US)

(73) Assignee: SULLY.AI, Santa Clara, CA (US)

( * ) Notice: Subject to any disclaimer, the term of this patent is extended or adjusted under 35 U.S.C. 154(b) by 0 days.

(21) Appl. No.: 18/902,532

(22) Filed: Sep. 30, 2024

Related U.S. Application Data

(63) Continuation-in-part of application No. 18/823,175, filed on Sep. 3, 2024.

(51) Int. Cl.
| | |
|---|---|
| *G16H 80/00* | (2018.01) |
| *G16H 10/60* | (2018.01) |
| *G16H 15/00* | (2018.01) |
| *G16H 20/00* | (2018.01) |

(52) U.S. Cl.
CPC ............ *G16H 80/00* (2018.01); *G16H 15/00* (2018.01); *G16H 10/60* (2018.01); *G16H 20/00* (2018.01)

(58) Field of Classification Search
CPC ........ G16H 80/00; G16H 15/00; G16H 10/60; G16H 20/00
See application file for complete search history.

(56) References Cited

U.S. PATENT DOCUMENTS

| | | | |
|---|---|---|---|
| 9,824,188 B2 | 11/2017 | Brown et al. | |
| 11,843,565 B2 | 12/2023 | Lee et al. | |
| 11,977,854 B2 | 5/2024 | Tunstall-Pedoe et al. | |
| 2019/0122766 A1* | 4/2019 | Strader | G16H 40/63 |
| 2020/0152302 A1* | 5/2020 | Co | G16H 70/20 |

(Continued)

FOREIGN PATENT DOCUMENTS

WO    WO-2022219627 A1 * 10/2022 ............. G16H 10/20

OTHER PUBLICATIONS

Malgaroli et al., Natural language processing for mental health interventions: a systematic review and research framework, Oct. 6, 2023, Translational Psychiatry, pp. 1-17 (Year: 2023).*

(Continued)

*Primary Examiner* — Christopher L Gilligan
(74) *Attorney, Agent, or Firm* — Flagship Patents; Shiv S. Naimpally; Sikander M. Khan

(57) ABSTRACT

In some aspects, an artificial intelligence (AI) performs an analysis of a conversation between a doctor and a patient, determines a first trigger phrase in the conversation, and determines a template of a patient visit note based on the first trigger phrase. The AI determines a second trigger phrase in the conversation, determines a particular treatment plan from a plurality of treatment plans based on the second trigger phrase, and adds the particular treatment plan to the template. A first instance of the AI adds a first portion of the conversation to the template and a second instance of the AI, in parallel with the first portion of the conversation being added to the template, adds a second portion of the conversation to the template. The AI provides the template of the patient visit note to a device associated with the doctor.

20 Claims, 13 Drawing Sheets

(56) References Cited

U.S. PATENT DOCUMENTS

| | | | |
|---|---|---|---|
| 2022/0059224 A1 | 2/2022 | Tulley et al. | |
| 2022/0148689 A1* | 5/2022 | Gill | G16H 10/60 |
| 2022/0172725 A1 | 6/2022 | Khan Khattak et al. | |
| 2023/0051982 A1 | 2/2023 | Sasidharan et al. | |
| 2023/0057949 A1* | 2/2023 | Tallent | G16H 40/20 |
| 2023/0385021 A1* | 11/2023 | Adams | G06F 3/167 |
| 2024/0281594 A1* | 8/2024 | Rao | G06F 40/166 |
| 2024/0395379 A1 | 11/2024 | Reani | |

OTHER PUBLICATIONS

Biao et al, Root Mean Square Layer Normalization, School of Informatics, University of Edinburgh, Retrieved on Jun. 6, 2024, 12 pages. [NeurIPS 2019].

Gao et al. Retrieval-Augmented Generation for Large Language Models: A Survey, Shanghai Research Institute for Intelligent Autonomous Systems, Tongji University, Mar. 27, 2024, 21 pages. [Url: arXiv:2312.10997].

Karan et al, Large Language Models Encode Clinical Knowledge, Google Research, Dec. 26, 2022, 44 pages. [arXiv:2212.13138].

Peter et al, Benefits, Limits, and Risks of GPT-4 as an AI Chatbot for Medicine. The New England Journal of Medicine, Mar. 30, 2023, 7 pages [N ENGL MED 388;13].

Tao et al, Towards Conversational Diagnostic AI, Google Research, Jan. 11, 2024, 46 pages. [arXiv:2401.05654].

Yu et a,l. Leveraging Generative AI and Large Language Models: AComprehensive Roadmap for Healthcare Integration, Oct. 20, 2023, Healthcare, pp. 1-19. (Year: 2023).

* cited by examiner

ARTIFICIAL INTELLIGENCE (AI) TO CREATE A PATIENT VISIT NOTE BASED ON A CONVERSATION BETWEEN A DOCTOR AND A PATIENT

RELATED APPLICATIONS AND DOCUMENTS

This application is a continuation-in-part of U.S. patent application Ser. No. 18/823,175, entitled, "ARTIFICIAL INTELLIGENCE (AI) TO PROVIDE DECISION SUPPORT INSIGHTS INCLUDING WHILE A DOCTOR IS ENGAGED IN CONVERSATION WITH A PATIENT,", filed on Sep. 3, 2024, which is hereby incorporated by reference herein in its entirety for all purposes as if fully set forth herein.

BACKGROUND

Field of the Technology

The technology disclosed relates to artificial intelligence type computers and digital data processing systems and corresponding data processing methods and products for emulation of intelligence (i.e., knowledge-based systems, reasoning systems, and knowledge acquisition systems); and including systems for reasoning with uncertainty (e.g., fuzzy logic systems), adaptive systems, machine learning systems, and artificial neural networks. In particular, the technology disclosed relates generally to systems and techniques to use an artificial intelligence (AI) to create a patient visit note based on conversation data (e.g., audio data or a text-based transcript) associated with a conversation between a doctor and a patient.

Description of the Related Art

Currently, when a patient visits a doctor, the doctor has a conversation with the patient in which the doctor asks questions and the patient provides responses. After the doctor has completed conversing with the patient, the doctor typically prepares a note, such as a Subjective, Objective, Assessment, and Plan (SOAP) note or similar, summarizing the doctor's observations, assessment, and plan for treatment. Preparing such a note is time consuming and reduces the time the doctor has available to see patients.

SUMMARY OF THE TECHNOLOGY DISCLOSED

This Summary provides a simplified form of concepts that are further described below in the Detailed Description. This Summary is not intended to identify key or essential features and should therefore not be used for determining or limiting the scope of the claimed subject matter.

In some aspects, an artificial intelligence (AI) performs an analysis of a conversation between a doctor and a patient, determines a first trigger phrase in the conversation, and determines a template of a patient visit note based on the first trigger phrase. The AI determines a second trigger phrase in the conversation, determines a particular treatment plan from a plurality of treatment plans based on the second trigger phrase, and adds the particular treatment plan to the template. A first instance of the AI adds a first portion of the conversation to the template and a second instance of the AI, in parallel with the first portion of the conversation being added to the template, adds a second portion of the conversation to the template. The AI provides the template of the patient visit note to a device associated with the doctor.

BRIEF DESCRIPTION OF THE DRAWINGS

A more complete understanding of the present disclosure may be obtained by reference to the following Detailed Description when taken in conjunction with the accompanying Drawings. In the figures, the left-most digit(s) of a reference number identifies the figure in which the reference number first appears. The same reference numbers in different figures indicate similar or identical items.

DETAILED DESCRIPTION

Figure 1:
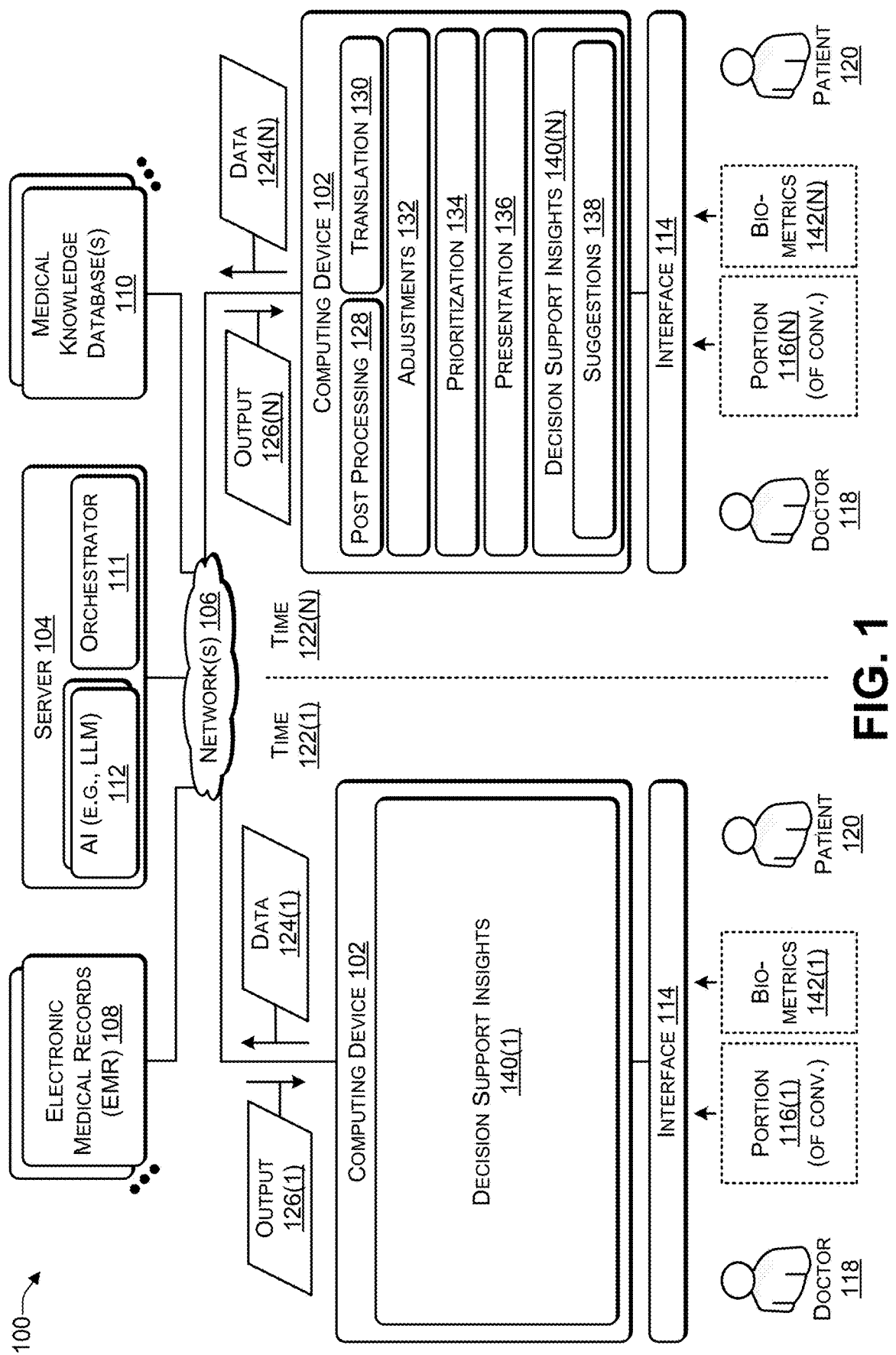
FIG. 1 is a block diagram of a system illustrating an artificial intelligence (AI) receiving a portion of a conversation between a doctor and a patient and generating decision support insights for the doctor, according to some implementations.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

The term "turn" references each piece of content communicated by one party (e.g., a doctor) in a conversation with at least one other party (e.g., a patient). For example: Doctor: "Hello. What is the reason for your visit?" (turn 1), Patient: "I have a burning sensation when I urinate." (turn 2), Doctor: "How frequently does this occur?" (turn 3), Patient: "Almost every time I urinate, especially at night." (turn 4), Doctor "That might be a bladder inflammation, a urinary tract infection (UTI), or a prostrate infection." (turn 5), etc.

The systems and techniques described herein provide a set of artificial intelligence (AI) enabled tools for doctors that provide insights and suggestions while the doctor is in conversation with the patient and drafts a Subjective, Objective, Assessment, and Plan (SOAP) note (or similar) summarizing the visit. In this way, the systems and techniques save the doctor time during day-to-day tasks that currently take up much of the doctor's time, e.g., tasks that do not involve seeing patients. While the doctor is in conversation with the patient, the AI may access the patient's electronic medical records (EMR) and repositories of medical knowledge to provide decision support insights, such as suggesting questions for the doctor to ask, suggesting possible diagnoses, suggesting one or more tests to be performed, suggesting a referral to a specialist, performing insurance-related tasks (e.g., looking up appropriate codes) and the like. After the AI determines that the doctor-patient conversation has ended, the AI may document the patient visit, including creating a SOAP note or similar. The note may be created using an off-the-shelf (OTS) template or using a custom template specified by the doctor. The summary of the visit may include a list of potential follow-up actions, such as scheduling a test (e.g., lab work), sending a referral, scheduling a follow-up appointment, and the like. The doctor can review, select, and initiate one or more of the follow-up actions with a few mouse clicks rather than having to manually enter the follow-up actions. For example, the doctor may have a particular specialist (e.g., cardiologist) to whom the doctor refers patients with particular symptoms (e.g., high-blood pressure). In this example, the AI determines, based on the conversation and the patient's medical history, that the patient may have high-blood pressure and predicts based on the doctor's history that the doctor may refer the patient to a cardiologist. The AI may automatically create a referral for the patient to see a particular cardiologist that the doctor prefers and display the referral action in a note summarizing the patient's visit. The referral action displayed in the note enables the doctor to send the referral with a single selection (e.g., via a mouse or other input device), thereby significantly reducing the time spent by the doctor to create and send the referral.

In some cases, the AI may be a generative AI, such as a large language model (LLM) or similar. The AI may include a commercially available AI (e.g., Chat GPT) and may, in some cases, be a hybrid multi-component AI that includes a custom AI (e.g., Orchestrator) and a commercially available AI (e.g., Chat GPT).

The AI may execute on a physical or cloud-based server and send decision support insights via a network to a computing device that is local to the doctor (e.g., a tablet, laptop, or desktop computing device located in the room with the doctor and patient). A multi-modal interface may listen in on the conversation between the doctor and patient and send either audio or a text-based transcription to the AI for analysis. For video and/or audio (telehealth) calls where the doctor and patient are not physically co-located, the interface may listen in to the audio of the conversation (audio or video call) between the doctor and the patient.

Thus, the AI may work in the background by ingesting portions (e.g., one or more turns) of the doctor-patient conversation and generating decision support insights based on the patient's medical history (derived from electronic medical records) and established medical knowledge. The decision support insights may include suggestions provided to the doctor in real-time, such as questions the doctor could ask the patient to confirm or rule out particular diagnoses, possible diagnoses (e.g., ranked from most likely to least likely) based on the patient's medical history and current medical knowledge, one or more tests to be performed to confirm or rule out particular diagnoses, a referral to a specialist, and the like. In addition, the doctor may explicitly interact with the AI using a "wake word", such as "Sully" (e.g., similar to "Siri", "Alexa", "Google" or other wake words used to interact with a virtual assistant). For example, the doctor may ask the AI "Sully, does the patient's history indicate that the patient underwent a cardiac ablation?". The AI is able to quickly respond to such questions because the AI has access to the patient's medical records, thereby saving the doctor time from having to perform a manual search of the patient's medical records. For example, the doctor may be seeing the patient for the first time but the patient may have had a previous doctor in another city or state and may have recently moved and so the doctor may be unfamiliar with the patient's complete medical history. As another example, the doctor may use the AI to ascertain information about the patient's history if the patient has difficulty responding to questions because the patient has a medical condition (e.g., autism, suffered a stroke, speech impediment, memory loss, or the like), has a poor grasp of the language in which the doctor communicates, is very young (e.g., a child), or due to another issue. In some cases, the systems and techniques may include a translation module to perform translation to and from a particular language (e.g., Spanish, French, or the like). The AI has access to a large pool of data, including each patient's historical data, such as electronic health records (EHR) and other patient data as well as previous doctor-patient conversations associated with the patient.

The systems and techniques may assist the doctor by generating documentation of a patient visit. After a patient comes in, the patient and the doctor have a conversation which the AI processes. After the AI determines that the patient visit has ended, the AI summarizes the visit by generating a note that is added to the EHR. The AI provides real-time decision support (something that current systems don't do) by listening to the conversation, looking at the patient's history, and generating in real-time suggestions for the doctor, such as what (next) questions the doctor should ask the patient, what might be possible treatment(s), differential diagnosis (to determine a root cause of the issue), possible referrals, possible tests to perform on the patient, and the like. After the visit, the AI creates a note (e.g., SOAP) summarizing the visit and a list of possible actions, such as referrals, lab orders, prescription(s), follow-up appointments, and the like. Without the AI, the doctor would have to review his/her notes, manually create the list of actions, and initiate the actions. By using the systems and techniques, the AI creates the list of actions and the doctor reviews them, selects a subset of the actions, and instructs the AI to perform the selected actions, including any action that a doctor currently performs after a patient visit.

The systems and techniques provide features of a virtual assistant to the doctor. For example, the assistant features may include medical assistant (MA) and research assistant (RA). To illustrate, the doctor sees a patient at a time T1 for which the AI creates a first note. The doctor then sees the patient again for a follow-up at a time T2 for which the AI creates a second note. If the visits are related, the doctor may ask the AI to merge the first note and the second note. The AI is able to determine what to carry forward from the first note, what to discard, and what to replace in first note (e.g., with information from the second note). For example, the patient recently had hip surgery. The first note is a post-surgery exam and says that the hip looks good with no apparent infection. The second note is a follow-up visit in which the doctor notes that while the patient's mobility is good, there is some redness and inflammation in the right hip. Thus, portions ("redness and inflammation") of the second note are used to replace portions ("looks good") of the first note. All conversations and note modifications are logged to provide an audit trail. The systems and techniques are able to provide the various functions described herein very quickly, in real-time, and with a high degree of accuracy.

After the AI determines the doctor-patient conversation has ended, the AI may generate a note (e.g., SOAP or similar) summarizing the visit based on the conversation. The note may be split into multiple parts based on a template. The template may be an off-the shelf (OTS) template provided by a service provider that licenses the AI to the doctor or the template may be a custom template specified by the doctor. For example, an ear, nose, throat (ENT) doctor may have a first template for patients with ear issues, a second template for patients with nose issues, and a third template for patients with throat issues.

To increase an accuracy of the note, the information from the conversation may be split into multiple parts (e.g., based on a doctor specified template), with the AI generating each of the multiple parts. In some cases, the multiple parts may be generated in parallel using multiple instances of the AI. For example, one of the parts may be a history of present illness (HPI). To reduce pollution in individual parts of the note, such as the HPI, a verification AI (e.g., LLM) may be trained to perform verification of each of the parts of the note. Thus, the template may be used to split the conversation-related data into multiple parts, with multiple instances of the AI generating each of the multiple parts in parallel. Individual verification AIs from a set of multiple verification AIs may be used to verify each portion of the note. For example, a particular verification AI may be trained to perform verification of the HPI portion of the note. Because the verification AI is designed to verify (rather than generate), the verification AI is able to perform the task of verification very quickly to enable the note (having multiple parts) to be generated and verified quickly (typically within a few seconds). The verification LLM is able to perform verification much faster than the AI takes to generate each part of the note. The verification AI may be given as input (1) a transcript of the conversation and (2) the part (e.g., HPI) that was generated by the AI. For example, a portion of the note may include billing codes. In this example, the AI generates (predicts) a billing code while the verification AI verifies that the billing code is correct, by determining if certain words associated with the billing code are mentioned in the transcript. The verification AI is low latency but improves the quality of each part of the note. The number of parts of the note may vary based on the doctor. For example, in some cases, note generation may be split into 5 parts—(1) generate HPI, (2) generate subjective exam, (3) generate assessment, (4) generate plan, and (5) generate patient instructions. Without the AI, the doctor would manually type all of this in to the system, typically several minutes per patient. In some cases, the AI may perform dynamic splitting. The AI may review the selected template (e.g., in the case of a custom template) and dynamically determine how to split the template into multiple parts. The AI dynamically splits the template to create multiple parts, generates the multiple parts, uses the multiple verification AI to verify each of the parts, and then merges the verified parts to create the note. The splitting and verification is used to address the challenge of providing low latency, high quality (e.g., high accuracy) results.

Another challenge when providing downstream decision support insights is how to display the insights to the doctor in a way that doesn't cause the doctor cognitive overload. The systems and techniques described herein use several techniques to display the decision support insights in such a way as to reduce cognitive overload. First, the AI determines an importance (e.g., criticality) of each decision support insight AI and displays insights having an importance greater than a predetermined threshold while suppressing (not displaying) insights having an importance less than or equal to the predetermined threshold. Every insight provided to the doctor has an internally associated importance and this may be used by the user interface (UI) to determine whether to display the insight and if so, how to display the insight. For example, extremely important insights (e.g., suggestions) may be presented using particular properties (e.g., highlight, bold, larger font, different font color, or the like) to highlight the suggestion to the doctor. For example, if the doctor, during the conversation with the patient, says "I will prescribe penicillin" and the patient's history has an indication of an allergic reaction to penicillin then the doctor may be visually alerted "Patient had a reaction to penicillin on <date>". The AI may provide the doctor with suggested questions to ask the patient. For example, the patient has knee pain and the doctor is asking the patient questions. The AI discovers, in the patient's medical history, that the patient had knee surgery on a previous date and suggests that the doctor ask questions related to the surgery. If the AI sends a suggestion for a question while the doctor is asking the same or a similar question, then the AI detects that the question has been asked and sends an update to remove the question and, in some cases, suggests one or more additional follow up questions. If the AI sends a suggestion for a question while the patient volunteers a response to the question, then the AI detects that the question has been answered and sends an update to remove the question and, in some cases, suggests one or more additional follow up questions.

In some cases, the internal importance of an insight may be determined based on a risk (predicted by the AI) and if more than one insight is to be presented to the doctor, the insights may be ranked by the AI according to risk, with the highest risk (most important) insight ranked first and the lowest risk (least important) insight ranked last. Of course, insights with an associated risk below a predetermined threshold may not be displayed. If the doctor misses an important insight when it is first displayed, the AI may adjust the particular properties (e.g., highlight, bold, larger font, different font color, or the like) of the insight to highlight the suggestion to the doctor. In some cases, the insight may be progressively highlighted (e.g., larger font in each subsequent iteration) until the doctor indicates (e.g., verbally or via an input device of a computer) that the doctor has seen the insight.

As previously mentioned, the AI may be a hybrid multi-component AI that includes a custom AI (e.g., Orchestrator) and a commercially available AI (e.g., Chat GPT). Historical data, including electronic medical records (EMR) may be provided as input to the AI. In some cases, at least a portion of the patient data may be fed in real-time to the AI. In some cases, doctor-patient conversations associated with a particular doctor may be used to train the AI to enable the AI to chat in a manner similar to the particular doctor. Thus, a doctor's own conversations with patients, CHAT GPT's regular training, and patient EMR records may all be used to train the AI. Complex business logic may be included in a prompt engineering layer of the AI to generate prompts dynamically, verify the output of the AI, and so on. In this way, the AI is able to react in real-time to a doctor-patient conversation.

In some cases, training the AI may include automatic prompt optimization in which a prompt is provided to the AI, the AI generates output, and the same AI model (or a different AI model) rewrites the prompt and looks at the output until a delta between an output and a subsequent output (from the rewritten prompt) is below a threshold.

The systems and techniques include an application programming interface (API) that sits between the AI (LLM) and an endpoint (e.g., a computing device located in the same room as the doctor and patient or tapped into a conversation between the doctor and the patient during a telehealth call). The API takes the doctor-patient conversation as input, sends it to the AI which processes the conversation data and provides outputs, including the decision support insights during the doctor-patient conversation and a note summarizing the conversation after the doctor-patient session has ended.

As a first example, a computer-implemented method include performing an analysis, using an artificial intelligence (AI), of a conversation between a doctor and a patient. In some cases, the artificial intelligence comprises a large language model. For example, the conversation between the doctor and the patient may include a text-based transcription that is created using a speech-to-text converter. The computer-implemented method includes determining, based at least in part on the analysis, a first trigger phrase in the conversation. The computer-implemented method includes determining a template of a patient visit note. The template is associated with the first trigger phrase. The computer-implemented method includes determining, based at least in part on the analysis, a second trigger phrase in the conversation. The computer-implemented method includes determining a particular treatment plan from a plurality of treatment plans based at least in part on the second trigger phrase. The computer-implemented method includes adding the particular treatment plan to the template. The computer-implemented method includes adding a first portion of the conversation to the template using a first instance of the artificial intelligence. The computer-implemented method includes adding a second portion of the conversation to the template using a second instance of the artificial intelligence in parallel with adding the first portion of the conversation to the template. The computer-implemented method may include verifying a first section of the template using a first verification artificial intelligence and verifying a second section of the template using a second verification artificial intelligence, in parallel with verifying the first section of the template. The computer-implemented method may include generating, by the artificial intelligence, one or more billing codes based on the analysis of the conversation and adding the one or more billing codes to the patient visit note. The computer-implemented method includes providing the template of the patient visit note to a device associated with the doctor. In some cases, the patient visit note includes at least: a subjective section, an objective section, an assessment section, and a plan section. For example, the plan section may include at least one of: a physical therapy session, a surgery, dietary restrictions, an exercise regimen, one or more over-the-counter supplements, one or more prescription drugs, a referral to another doctor, or any combination thereof.

As a second example, a server includes one or more processors and one or more non-transitory computer-readable storage media to store instructions that are executable by the one or more processors to perform various operations. The operations include performing, by an artificial intelligence, an analysis of a conversation between a doctor and a patient. The operations include determining, based at least in part on the analysis, a first trigger phrase in the conversation. The operations include determining a template of a patient visit note. The template is associated with the first trigger phrase. The operations include determining, based at least in part on the analysis, a second trigger phrase in the conversation. The operations include determining a particular treatment plan from a plurality of treatment plans. The particular treatment plan is associated with the second trigger phrase. The operations include adding the particular treatment plan to the template. The operations include adding a first portion of the conversation to the template using a first instance of the artificial intelligence and adding a second portion of the conversation to the template using a second instance of the artificial intelligence. The second portion of the conversation is added to the template in parallel with the first portion of the conversation being added to the template. The first portion of the conversation may include one or more of: a chief complaint associated with the patient, a history of a present illness associated with the patient, or at least a portion of a medical history associated with the patient. The second portion of the conversation may include a diagnosis expressed by the doctor during the conversation. The operations may include verifying a first section of the template using a first verification artificial intelligence and verifying a second section of the template using a second verification artificial intelligence in parallel with verifying the first section of the template using the first verification artificial intelligence. In some cases, the operations may include adding one or more biometric measurements associated with the patient to the template. For example, the one or more biometric measurements may include at least one of: a body temperature, a diastolic blood pressure measurement, a systolic blood pressure measurement, a pulse rate, a blood oxygen level, an electro-cardiogram, or any combination thereof. The operations include providing the template of the patient visit note to a device associated with the doctor. In some cases, the patient visit note includes at least: a subjective section, an objective section, an assessment section, and a plan section. For example, the plan section may include: a physical therapy session, a surgery, dietary restrictions, an exercise regimen, one or more over-the-counter supplements, one or more prescription drugs, a referral to another doctor, or any combination thereof.

As a third example, a non-transitory computer-readable storage medium is used to store instructions that are executable by one or more processors to perform various operations. The operations include performing, by an artificial intelligence, an analysis of a conversation between a doctor and a patient. The operations include determining, based at least in part on the analysis, a first trigger phrase in the conversation. The operations include determining a template of a patient visit note, where the template is associated with the first trigger phrase. The operations include determining, based at least in part on the analysis, a second trigger phrase in the conversation. The operations include determining a particular treatment plan from a plurality of treatment plans, where the particular treatment plan is associated with the second trigger phrase. The operations include adding the particular treatment plan to the template. The operations include adding a first portion of the conversation to the template using a first instance of the artificial intelligence. The operations include adding a second portion of the conversation to the template using a second instance of the artificial intelligence. The second portion of the conversation is added to the template in parallel with the first portion of the conversation being added to the template. The operations may include verifying a first section of the template using a first verification artificial intelligence and verifying a second section of the template using a second verification artificial intelligence in parallel with verifying the first section of the template. The operations may include generating, by the artificial intelligence, one or more billing codes based on the analysis of the conversation; and adding the one or more billing codes to the patient visit note. The operations may include adding one or more biometric measurements associated with the patient to the template. For example, the one or more biometric measurements may include at least one of: a body temperature, a diastolic blood pressure measurement, a systolic blood pressure measurement, a pulse rate, a blood oxygen level, an electro-cardiogram, or any combination thereof. The operations include providing the template of the patient visit note to a device associated with the doctor. For example, the patient visit note may include at least: a subjective section, an objective section, an assessment section, and a plan section. The plan section may include at least one of: a physical therapy session, a surgery, dietary restrictions, an exercise regimen, one or more over-the-counter supplements, one or more prescription drugs, a referral to another doctor, or any combination thereof.

FIG. 1 is a block diagram of a system 100 illustrating an artificial intelligence (AI) receiving a portion of a conversation between a doctor and a patient and generating decision support insights for the doctor, according to some implementations. The system 100 includes a computing device 102 connected to a server 104 via a one or more networks 106. The server 104 may access one or more electronic medical records (EMR) 108 via the network 106. The server 104 may access one or more medical knowledge databases 110 via the network 106. The server 104 includes an orchestrator 111 and one or more artificial intelligence (AI) 112. In some cases, the AI 112 may be implemented using a generative AI, such as a large language model (LLM) or similar.

FIG. 1 illustrates the interaction between the computing device 102 and the server 104 at two different times, at a time 122(1) and at a time 122(N) (N>1) that occurs after the time 122(1). The events that occur at the time 122(N) are referred to as downstream relative to events that occur at the time 122(1). The events that occur at the time 122(1) are referred to as upstream relative to events that occur at the time 122(N).

The computing device 102 may be a tablet computing device, a laptop, a desktop, a smart phone, or another type of computing device that a doctor 118 uses when seeing patients, such as a representative patient 120. If the patient 120 has indicated a reason as to why the patient 120 has made an appointment with the doctor 118, the AI 112 may determine the reason by accessing the electronic medical records 108. The AI 112 may access the electronic medical records 108 associated with the patient 120 to determine the patient's medical history. The AI 112 may access the medical knowledge database 110 regarding information relevant to the patient's reason for visiting the doctor and relevant to the patient's medical history. Based on the reason for the patient's visit, the patient's history, and the medical knowledge in the medical knowledge databases 110, the AI 112 may provide output 126(1) to the computing device 102 that is displayed as a decision-support insight 112(1). For example, if the patient's reason for the current visit to the doctor 118 is lower back pain and the patient's history, accessed via the EMR 108, indicates a history of back pain, then the decision support insights 140(1) may include questions ("Are you stretching your hamstrings regularly?") to ask the patient 120 and a possible prescription (e.g., for a muscle relaxant that the patient has responded to in the past). In this way, the doctor 118 may enter the location where the patient 120 is located, review the decision support insights 140(1) and begin a conversation with the patient 120.

An interface 114 associated with the computing device 102 may capture a portion 116(1) of a conversation between the doctor 118 and the patient 120. For example, the portion 116(1) of the conversation may include one or more turns between the doctor 118 and the patient 120. The computing device 102 may receive the portion 116(1) from the interface 114 and send the data 124(1) to the server 104 for processing by the AI 112. The data 124(1) may be (1) audio data of the portion 116(1) of the conversation captured by a microphone of the interface 114, (2) a text-based transcript of the portion 116(1) created by a speech-to-text module executed by the computing device 102, or (3) any combination thereof. Of course, in some cases, the speech-to-text module may be executed by the server 104. In such cases, the computing device 102 may send audio data (in the data 124(1)) to the server 104 and the server 104 may convert the audio data to text for the AI 112 before using the text of the conversation as input. Thus, the AI 112 may be trained using text-based data, audio-based data, or a combination of both.

The interface 114 may capture biometrics 142 associated with the patient 120 such as, for example, blood pressure (from a blood pressure monitor), pulse (from a pulse rate monitor), electrocardiogram (ECG) data (from an ECG machine), temperature (from a thermometer), oxygen level (from an oximeter), and other biometric data. The interface 114 may include the biometrics 142 in the data 124 sent to the server 104.

The AI 112 receives the data 124(1) including the biometrics 142(1) and the portion 116(1) of the conversation between the doctor 118 and the patient 120 and produces raw output 126(N), including additional decision support insights 140(N), based on the data 124(1), the patient's history (as derived from the EMR 108), and the medical knowledge databases 110. For example, based on the data 124(1), the AI 112 may provide suggestions 138 that include one or more additional questions for the doctor 118 to ask the patient 120, suggest one or more tests (e.g., EKG or echocardiogram for heart-related issues) that the doctor 118 should consider performing on the patient 120, suggest one or more referrals (e.g., referral to a specialist, such as a cardiologist for heart-related issues, a gastroenterologist for digestive-related issues, an ophthalmologist for eye-related issues, and so on), suggested diagnoses (e.g., high blood pressure), suggested prescriptions (e.g., diuretic, calcium channel blocker, ace inhibitor, or angiotensin receptor blocker for high blood pressure), and the like. In some cases, the AI 112 may update the doctor on possible contraindications. For example, assume the patient 120 is describing symptoms related to high blood pressure and the doctor 118 is proposing to put the patient 120 on a diuretic. The AI 112 may determine, based on the patient's history, that the patient 120 has previously suffered from gout. The AI 112 may further determine, based on the medical knowledge databases 110, that a diuretic may cause a recurrence of gout. In such cases, the AI 112 may include, in the suggestions 138, an indication that the patient 120 has previously suffered from gout, an indication that the diuretic may cause the gout to recur and suggest an alternative blood pressure medication.

The computing device 102 may perform post processing 128 of the output 126(N) to derive and present one or more of decision support insights 140(N), adjustments 132, prioritization 134, presentation 136, and suggestions 138. In some cases, the computing device 102 may provide a translation 130 from one language (e.g., used by the doctor 118) to another language (e.g., used by the patient 120). For example, the translation 130 may perform (1) Spanish to English translation and (2) English to Spanish translation when the doctor 118 speaks English and the patient 120 speaks Spanish. While the post processing 128 and the translation module 130 are illustrated as being executed by the computing device 102, in some cases one or both of the post processing 128 and the translation 130 may be executed by the server 104.

The suggestions 138 may include questions for the doctor 118 to ask the patient 120, suggestions for one or more tests for the patient 120, suggestions for one or more referrals, suggested diagnoses, suggested prescriptions, and other insights derived from the portion 116(1), the EMR 108, and the medical knowledge databases 110. In some cases, the output 126(N) may specify one or more adjustments 132 to previously provided decision support insights, such as the decision support insights 140(1). For example, the portion 116(1) of the conversation may cause the AI 112 to provide a particular suggestion. At approximately the same time, the particular suggestion may occur to the doctor 118. The doctor 118 may utter the particular suggestion (e.g., a particular diagnoses, a particular question, or the like) in a subsequent portion 116 (e.g., the portion 116(N)) of the conversation. After receiving the subsequent portion 116 of the conversation that includes the particular suggestion, the AI 112 may determine that the doctor 118 has provided the particular suggestion and include in the adjustments 132 an instruction to delete the particular suggestion from the suggestions 138 or the decision support insights 140(N) displayed to the doctor 118. As another example, the portion 116(1) of the conversation may cause the AI 112 to provide a particular suggestion. At approximately the same time, the patient 120 may volunteer information related to particular suggestion in a subsequent portion 116 of the conversation. For example, assume the particular suggestion includes a question for the doctor 118 to ask the patient 120 and the patient, during the subsequent portion 116 of the conversation, volunteers (e.g., without the doctor 118 asking) the answer to the question. After receiving the subsequent portion 116 of the conversation that includes the answer to the question, the AI 112 may determine that the doctor 118 no longer should ask the question and include in the adjustments 132 an instruction to delete the particular suggestion (to ask the question) from the suggestions 138 or the decision support insights 140(N) displayed to the doctor 118. In these examples, the AI 112 may determine that a suggestion to ask the patient a particular question can be removed because either the doctor 118 asked the question or the patient 120 volunteered information answering the question. To illustrate, if the doctor 118 determines that the patient 120 is likely suffering from high blood pressure and is considering prescribing a diuretic, the AI 112 may provide in the suggestions 138 that the doctor 118 ask the patient 120 if the patient has previously suffered from gout. Before or while the suggestions 138 are being displayed by the computing device 102, the doctor 118 may ask the patient 120 whether the patient 120 has previously suffered from gout. Alternately, before or while the suggestions 138 are being displayed by the computing device 102, the patient 120 may volunteer that the patient 120 has previously suffered from gout. In either case, the AI 112 determines that the suggestion to the doctor 118 to ask the patient 120 the question (whether the patient 120 has previously suffered from gout) is no longer applicable and includes an instruction in the adjustments 132 to remove that particular question from the suggestions 138 or the decision support insights 140(N).

The prioritization 134 may prioritize the suggestions 138, the decision support insights 140(N) or both based on a criticality score assigned to each of the decision support insights 140(N) based on medical urgency. The prioritization 134 may occur in different ways based on presentation logic 136. The presentation logic 136 may include preferences of the doctor 118 on how the decision support insights 140(N) are presented. For example, the presentation logic 136 may reorder the suggestions 138 based on the criticality score such that suggestions with a higher score are placed higher while suggestions with the lower score are placed lower in the list of suggestions 138. As another example, the presentation logic 136 may color code the suggestions 138 based on the criticality score. In this example, suggestions with a higher score may be displayed with a particular color or font size compared with suggestions having a lower score. To illustrate, a critical suggestion may be displayed in a larger font or in bold font while less critical suggestions may be displayed in a smaller font or in a normal (non-bold) font. In this way, the presentation logic 136 may use the prioritization 134 to determine how and in what order the decision support insights 140(N) are displayed to the doctor 118, thereby enabling the doctor 118 to visually identify critical decision support insights.

Of course, the process may continue with another portion 116(N) of the conversation between the doctor 118 and the patient 120 being captured by the interface 114 and sent to the AI 112 as the data 124(N) for additional processing. Thus, the AI 112 may continually receive portions of the conversation between the doctor 118 and the patient 120 and continually provide the output 126 for display to the doctor 118 as the decision support insights 140. This process continues until the AI 112 determines that the conversation has ended, typically after determining that one or both of the doctor 118 or the patient 120 has left the room or is no longer participating in a telehealth call. As previously mentioned, the conversation between the doctor 118 and the patient 120 may occur physically in a room, such as an examination room associated with the doctor 118 or virtually via a telehealth call, such as a video call or an audio call. The AI 112 provides the output 126 to a display device associated with the computing device 102 that the doctor 118 can view but that the patient 120 may not view.

Thus, an interface may capture a portion (one or more turns) of a conversation between a doctor and a patient and send the captured portion, as audio data, transcribed text data, or both to an AI. The AI analyzes the captured portion of the conversation while accessing the electronic medical records associated with the patient's medical history as well as medical knowledge databases to provide decision support insights to the doctor during the conversation. The decision support insights may include suggested questions for the doctor to ask the patient, suggestions for one or more tests to be given to the patient, suggestions for one or more referrals to a specialist, possible contraindications, insights related to a differential diagnosis, suggested diagnoses, suggested prescriptions, and other similar AI-derived insights. These decision support insights are designed to support the doctor during the doctor's conversation with the patient by making the doctor aware of these insights based on conversation, the patient's medical history, and current medical knowledge.

Figure 2:
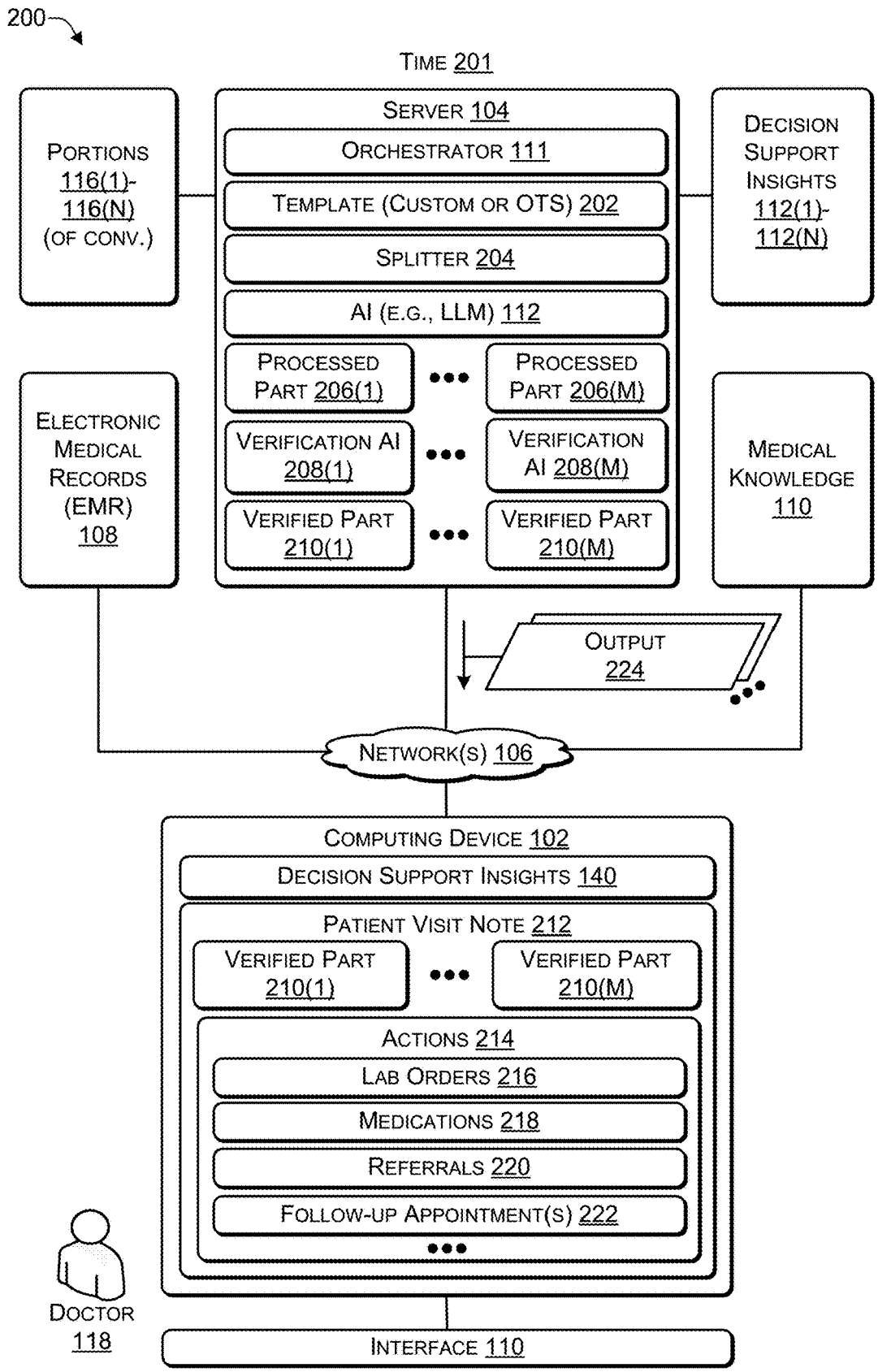
FIG. 2 is a block diagram of a system illustrating an artificial intelligence (AI) architecture creating a note (e.g., Subjective, Objective, Assessment, and Plan (SOAP) note) after a doctor has concluded a conversation with a patient, according to some implementations.

FIG. 2 is a block diagram of a system 200 illustrating an artificial intelligence (AI) architecture creating a note (e.g., a Subjective, Objective, Assessment, and Plan (SOAP) note or similar) after a doctor has concluded a conversation with a patient, according to some implementations. FIG. 2 illustrates what occurs after the AI 112 determines that the conversation between the doctor 118 and the patient 120 has ended, at a time 201. The time 201 occurs after the AI 112 determines that at least one of the doctor 118 or the patient 120 has left the room (e.g., examination room) or is no longer participating in a telehealth call and occurs after the time 122(N) of FIG. 1. The conversation between the doctor 118 and the patient 120, including portions 116(1) to 116(N), and the decision support insights 140(1) to 140(N), generated by the AI 112 in response to the conversation, may be used by the AI 112 to generate a patient visit note 212.

The orchestrator 111 may select a template 202 specified by the doctor 118. The template 202 may be an off-the-shelf (OTS) template selected by the doctor 118 or a custom template designed by the doctor 118. The orchestrator 111 may instruct a splitter module 204 to categorize the conversation portions 116 and the decision support insights 140 based on the template 202 to create processed parts 206(1) to 206(M) (M>0, typically 4 to 6). For example, when creating a SOAP note, the conversation portions 116 and the decision support insights 140 may be placed by the splitter 204 into 4 categories (Subjective, Objective, Assessment, and Plan).

Each category of the processed parts 206 may have a corresponding verification AI 208. For example, the processed part 206(1) may be verified by the verification AI 208(1) and the processed part 206(M) may be verified by the verification AI 208(M). Each of the verification AI 208 may be trained to perform verification of a particular portion of the patient visit note 212 to enable the verification to occur quickly (in real-time). The verification AI 208(1) to 208(M) may verify the processed parts 206(1) to 206(M) to produce verified parts 210(1) to 210(M), respectively. The verified parts 210(1) to 210(M) may be included in output 224 to the computing device 102.

Thus, the portions 116(1) to 116(N) of the conversation and the decision support insights 140(1) to 140(N) may be split into multiple parts 206 (e.g., based on a doctor specified template 202). The multiple parts 206(1) to 206(M) may be generated in parallel using multiple instances of the AI 112. For example, one of the parts 206 may be a history of present illness (HPI). To reduce pollution in individual parts of the note, such as the HPI, each of the verification AI 208 (e.g., LLM) may be trained to perform verification of a particular one of the parts of the patient visit note 212. In this way, the template 202 may be used to split the portions 116 and insights 140 into multiple parts 206, with multiple instances of the AI 112 generating each of the multiple parts 112 in parallel. Individual verification AIs 208 may be used to verify each of the processed parts 206. For example, a particular verification AI 208 may be trained to perform verification of the HPI part (one of the parts 206) of the note 212. Because each verification AI 208 is trained to verify, the note 112 (having multiple parts) can be generated and verified quickly (typically within a few seconds). The verification AI 208 may be able to perform verification much faster than the AI 112 takes to generate each of the processed parts 206. The verification AI 208 may use as input (1) a transcript of the portions 116 of the conversation and (2) the processed part 206 (e.g., HPI) that was generated by the AI 112. For example, a part 206 of the note 212 may include billing codes. The AI 112 generates (predicts) a billing code while the verification AI 208 verifies that the billing code is correct, by determining if certain words associated with the billing code are mentioned in the transcript of the portions 116 of the conversation. The verification AI 208 are low latency but improve the quality of each part of the note 212. The number of parts of the note 212 may vary based on the doctor. For example, in some cases, note generation may be split into 5 parts: (1) generate HPI, (2) generate subjective exam, (3) generate assessment, (4) generate plan, and (5) generate patient instructions. Without the AI 112, the doctor 118 may manually type all of this in to the computing device 102, typically taking at least several minutes per patient.

In some cases, the AI 112 and the splitter 204 may perform dynamic splitting. The AI 112 may review the selected template 202 and dynamically determine how to split the template 202 into multiple parts 206. The AI 112 uses the splitter 204 to dynamically split the template 202 to create multiple parts 206 and uses the multiple verification AI 208 to verify each of the parts 206, and then merges the verified parts 210 to create the note 212. The computing device 102 may receive the output 224 from the server 104 and create the patient visit note 212 and a set of selectable actions 214. The patient visit note 212 may include the verified data 210(1) to 210(M) organized according to the template 202.

The actions 214 may include suggested actions derived from the decision support insights 140(1) to 140(N), such as lab orders 216, medications 218, referrals 220, follow-up appointments 222, and other actions. The actions 214 may be selectable to enable the doctor 118 to select which of the actions 214 the doctor 118 desires to be performed. For example, the doctor 118 may select (1) a lab order to be sent to the lab for a comprehensive metabolic panel (CMP), (2) a new medication or a refill for an existing medication be sent to a pharmacy associated with the patient 120, (3) a referral letter be sent referring the patient 120 to a particular specialist (cardiologist, gastroenterologist, endocrinologist, or the like), schedule a follow-up appointment in six months, and so on. After selecting one or more of the actions 214 the doctor 118 can initiate the selected actions using the computing device 102. In this way, the doctor 118 avoids manually reviewing the doctor's notes to determine what further actions to take. Instead, the AI 112 provides a list of possible actions 214 derived from the decision support insights 140(1) to 140(N), enabling the doctor 118 to perform one or more of the actions 214 simply by selecting one or more of the actions 214 and instructing the computing device 102 to perform the selected actions.

Thus, after an AI determines that a conversation between a patient in a doctor has ended, the AI may create a patient visit note that summarizes the patient visit. For example, the note may be in the form of a SOAP or similar note. In addition, the AI may generate a set of actions, based on the decision support insights generated during the visit, to enable the doctor to quickly select and initiate one or more of the actions. In this way, the AI is able to save the doctor a significant amount of time because the doctor does not manually create the patient visit note and does not manually enter and initiate one or more actions.

Figure 3:
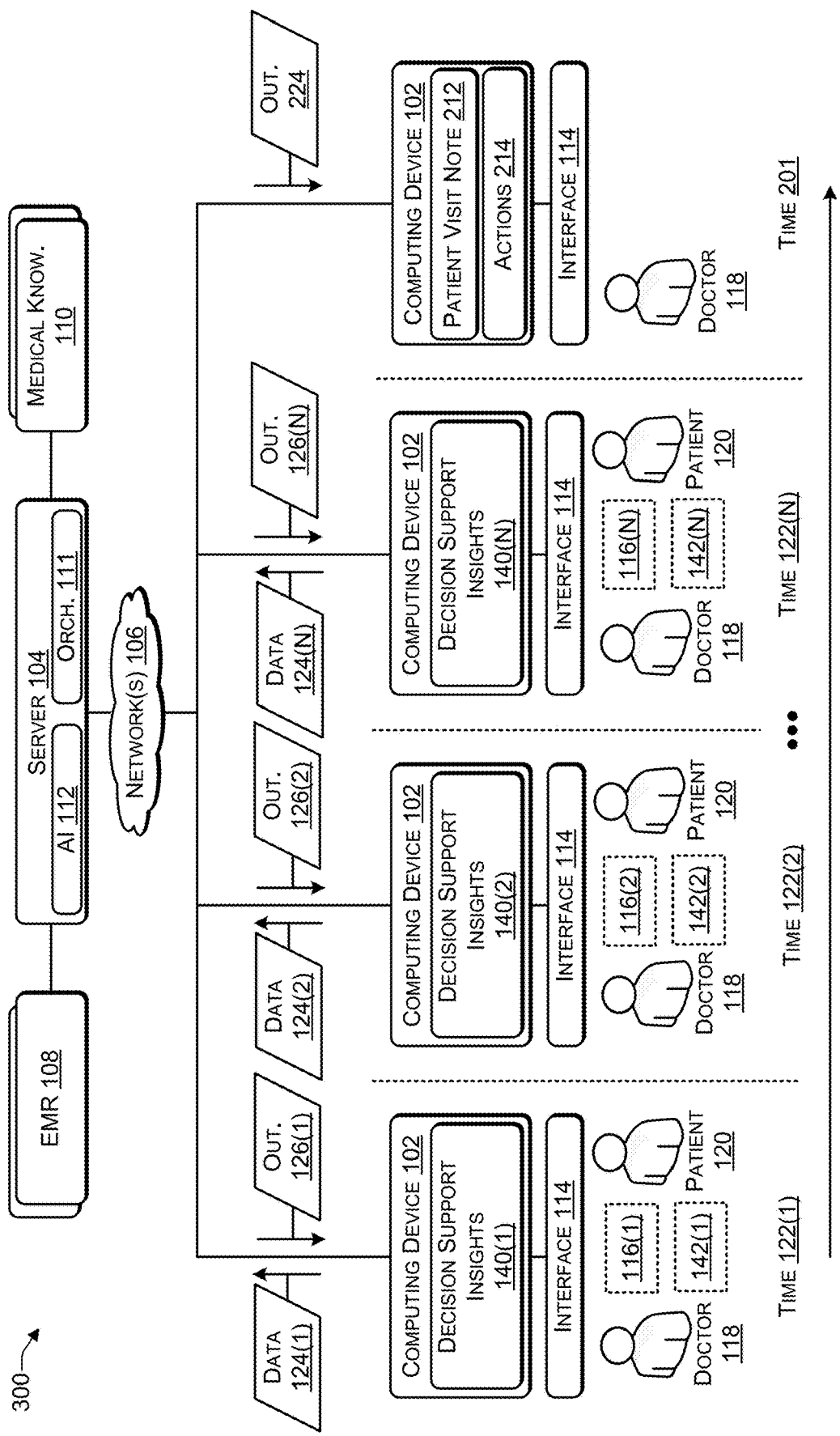
FIG. 3 is a block diagram of a timeline illustrating an artificial intelligence (AI) providing decision support insights to a doctor, according to some implementations.

FIG. 3 is a block diagram of a timeline 300 illustrating an artificial intelligence (AI) providing decision support insights to a doctor, according to some implementations. The timeline 300 illustrates when different events occur. For example, at the time 122(1), the patient 120 initially meets with the doctor 118. The computing device 102 displays the initial decision support insights 140(1). The computing device 102 gathers and sends the biometrics 142(1) (if available) and the portion 116(1) of the conversation between the doctor 118 and the patient 120 to the AI 112. At the time 122(2), the patient 120 continues the visit with the doctor 118. The computing device 102 displays the decision support insights 140(2) generated by the AI 112 and based on the portion 116(1) of the conversation, the EMR 108, and the medical knowledge 110. The computing device 102 gathers and sends the biometrics 142(2) (if available) and the portion 116(2) of the conversation between the doctor 118 and the patient 120 to the AI 112. The computing device 102 displays the decision support insights 140(N) generated by the AI 112 and based on the portion 116(N−1) of the conversation, the EMR 108, and the medical knowledge 110. The computing device 102 gathers and sends the biometrics 142(N) (if available) and the portion 116(N) of the conversation between the doctor 118 and the patient 120 to the AI 112. In some cases, the AI 112 may determine that the conversation between the doctor 118 and the patient 120 has ended based on the portion 116(N). For example, the portion 116(N) may include the doctor 118 and/or the patient 120 verbally indicating (e.g., "Goodbye", "See you in 6 months", or the like) that the conversation has ended. Thus, the AI 112 may look for a trigger phrase indicating that the conversation has ended. After the AI 112 determines that the conversation has ended or in response to a request from the doctor 118, the AI 112 may generate the patient visit note 212 and one or more follow-up actions 214.

Figure 4:
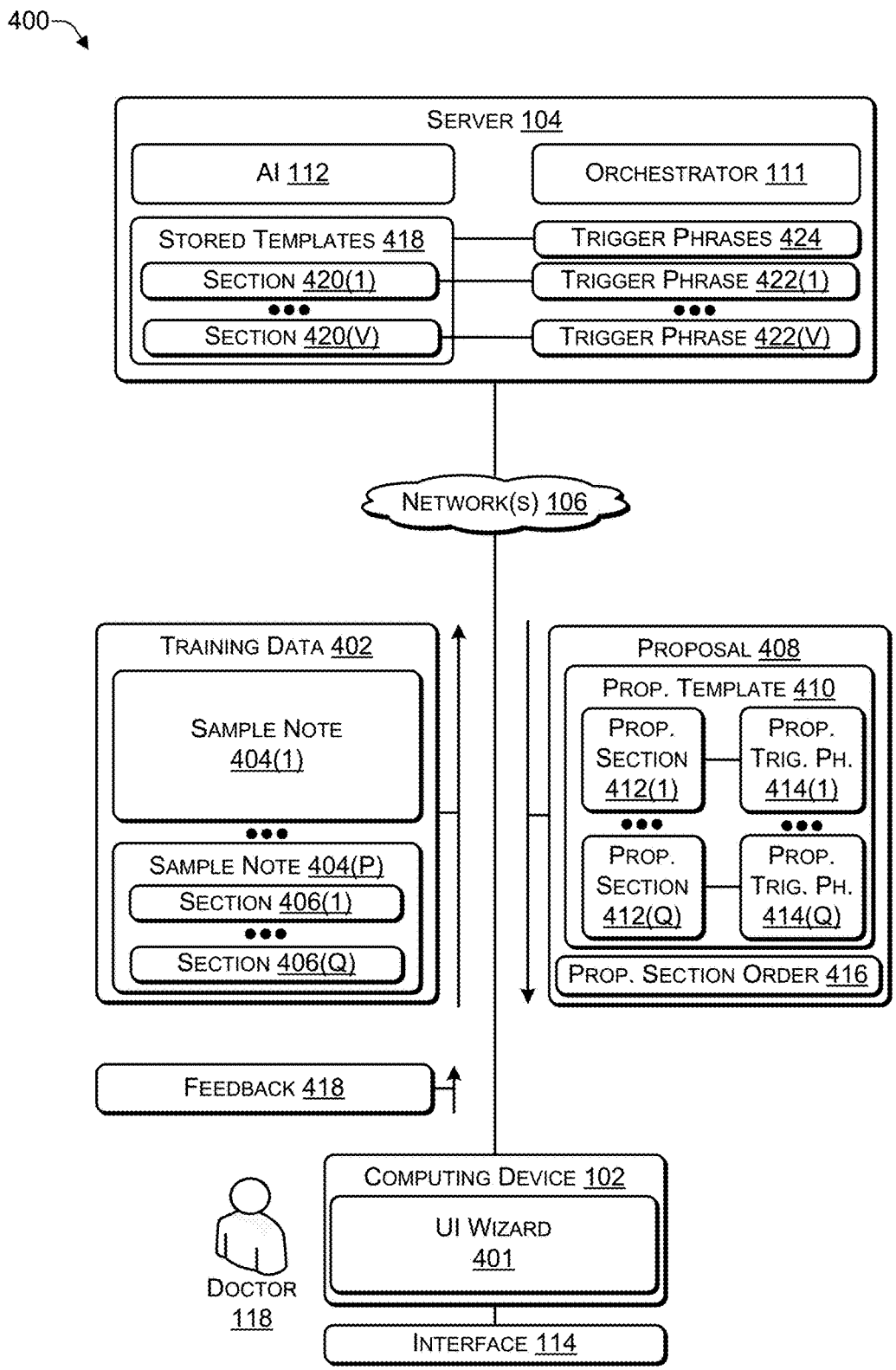
FIG. 4 is a block diagram of a system to create a template for a patient visit note in which one or more sections of the template have an associated trigger phrase, according to some implementations.

FIG. 4 is a block diagram of a system 400 to create a template for a patient visit note in which one or more sections of the template have an associated trigger phrase, according to some implementations. The doctor 118 may use a user interface (UI) wizard 401 to create a custom template. The UI wizard 401 may prompt the doctor 118 to provide information about the template, such as how many sections to create, ask the doctor to name each section, ask the doctor to provide an order of the sections, and so on. The UI Wizard may create a proposed template, received feedback from the doctor, and modify the proposed template, until the doctor approves of the proposed template.

In some cases, the doctor 118 may provide training data 402, including sample notes 404(1) to 404(P) (P>0), to the AI 112 for analysis. The sample notes 404 may include notes that the doctor 118 has previously filled out and that the doctor 118 is providing as samples to train the AI 112. Each of the sample notes 404 may include multiple sections, such as sections 406(1) to 406(Q) (Q>0). For example, one of the sample notes 404 may include a SOAP note or similar. While a SOAP note has four sections, the sample notes 404 may have less than four or more than four sections. The number of sections 406 may vary based on the type of the note 404. As another example, in the case of an ear, nose, throat (ENT) doctor, a first portion of the sample notes 404 may be associated with the ear, a second portion of the sample notes 404 may be associated with the nose, while a third portion of the sample notes 404 may be associated with the throat. As a further example, in the case of a sports medicine specialist, the sample notes 404 may include notes associated with particular sports injuries or particular parts of the body, e.g., a note for knee issues, a note for elbow issues, a note for rotator cuff injuries, and the like. Particular sections 406 may include requests for tests for the most common types of medical issues the doctor 118 encounters. For example, the tests may include a urine test, blood tests, such as fasting glucose, comprehensive metabolic panel, and the like and tests to screen for particular conditions (e.g., check for thalassemia minor, full thyroid panel to check for hypo-thyroid or hyper-thyroid, and the like). Particular sections 406 may include treatment plans, such as, for example, physical therapy, surgery, diet, exercise, one or more over-the-counter supplements, one or more prescription drugs, and other treatment plans for the most common types of medical issues that the doctor 118 encounters. The sections 406 may be hierarchical, e.g., a particular section may include one or more sections (e.g., sub-sections) and one or more of the sub-sections may include one or more sections and so on.

The AI 112 may perform an analysis of the training data 402, including the sample notes 404 and use the analysis to create a proposal 408 including a proposed template 410 that is based on the sample notes 404 and that includes proposed sections 412(1) to 412(Q). One or more of the proposed sections 412 may include an associated proposed trigger phrase 414. For example, the proposed section 412(1) may have an associated proposed trigger phrase 414(1) and the proposed section 412(Q) may have an associated proposed trigger phrase 414(Q). In some cases, one of the proposed trigger phrases 414 may include a trigger phrase associated with the proposed template 410. For example, when the AI 112 in analyzing the conversation between the doctor 118 and the patient 120 and identifies a particular trigger phrase, then the AI 112 may insert the associated section into the patient visit note (e.g., based on a template). In this way, by uttering a particular trigger phrase during the conversation, the doctor 118 causes the AI 112 to insert a particular section, such as a particular treatment plan or a particular test, into the patient visit note. The proposal 408 may include a proposed section order 416 for the proposed sections 412.

The doctor 118 may receive the proposal 408 and provide feedback 418. For example, in some cases, the feedback 418 may include modifications to the proposed template 410, including modifying (including adding and/or deleting) one or more of the proposed sections 412, modifying the proposed section order 416, modifying one or more of the trigger phrases 414, or any combination thereof. If the feedback 418 includes changes to the proposal 408, the AI 112 may modify the proposal 408 and send the modified proposal to the doctor 118 for review. This process of the AI 112 providing the proposal 408 and the doctor 118 reviewing the proposal 408 and providing the feedback 418 may continue until the feedback 418 indicates the doctor's approval. After receiving the doctor's approval in the feedback 418, the AI 112 may store the proposed template 410 as one of available templates 418. The templates 418 may include off-the-shelf templates created by a provider of the AI 112, default templates (e.g., SOAP or another type of standard template currently in use by many doctors), and custom templates, such as the proposed template 410, created and approved by the doctor 118. Each of the templates 418 may include a section, such as a section 420(1) to a section 420(V). At least some of the individual sections 420 may have an associated trigger phrase. For example, the section 420(1) may have an associated trigger phrase 422(1) and the section 420(V) may have an associated trigger phrase 422(V). In some cases, individual ones of the templates 418 may have an associated trigger phrase of the trigger phrases 424. Identifying a particular trigger phrase in the conversation may cause the AI 112 to select a particular template of the templates 418. For example, if the doctor 118 says "Let us get you started with a plan to address XYZ" then the AI 112 may select one of the templates 418 associated with XYZ (e.g., a condition, such as high blood pressure, high blood sugar, high cholesterol, tennis elbow, or the like). In this example, "XYZ" or "address XYZ" may be the trigger phrase associated with a particular template. In some cases, the template associated with XYZ may include one or more pre-filled sections, such as particular tests to be performed, particular treatment plans to perform, or both. For example, if XYZ is high blood pressure, the associated template may include follow-up visits every 3 months, a diet plan (e.g., low sodium), an exercise plan, a particular prescription medication (e.g., angiotensin receptor blocker (ARB)), and so on. As another example, if XYZ is high blood sugar, the associated template may include a diet plan (low sugar, low carbs), an exercise plan, a particular prescription medication (e.g., metformin), a fasting glucose test every 6 months or a prescription for a continuous glucose monitor (CGM), and so on.

Thus, in some cases, a UI wizard may prompt a doctor to create a template with multiple sections. In other cases, the doctor may provide sample notes which the AI analyzes and uses to create a proposed template. For example, if the doctor is a sports medicine specialist, the doctor may have a template for common conditions that the doctor treats, such as knee treatment, tendonitis, tennis elbow, and the like. Each condition may have a different template. Each doctor may have 100s of templates. Some sections may be relatively generic while other sections may be specific to particular conditions. Individual templates and individual sections may have an associated trigger phrase that causes the AI to select a particular template or add particular sections to a template. Each trigger phrase may cause the AI to select a particular template and/or insert a particular section into the template. SOAP is a default layout. A doctor may have a custom template with more than 4 sections and a custom layout. Thus, an AI may first ingest multiple user-provided templates. The AI may identify and associate a trigger phrase with each template and, in some cases, with one or more sections of the template. The AI may propose which trigger phrase is associated with which template and with which section and the doctor may modify or confirm the trigger phrases. During a conversation with a patient, the doctor can mention a particular trigger phrase, causing the AI to identify the appropriate template (for the patient visit note) and, in some cases, appropriate sections. just need to mention the trigger phrase, e.g., XYZ treatment (e.g., surgery, rehab, etc.). The AI may extract sections from multiple sample notes and determine an order of the sections in the note. The AI provides the proposed patient visit note structure to the doctor for review. The doctor may modify the proposed patient visit note structure by modifying one or more of the name of the template, name of individual sections, the number of sections, the section order, and trigger phrase associated with each section, and so on. In some cases, the doctor may modify the proposed template using voice commands that direct the AI to modify the proposed template. The AI receives the feedback from the doctor, modifies the proposed template, provides the modified proposed template to the doctor for review until the doctor indicates, in the feedback, that the doctor has approved the proposed template. Thus, the doctor can create custom templates by providing previously filled out patient visit notes as sample notes to an AI. The AI uses the sample notes to learn what sections the doctor uses. The AI determines an order of the sections in the template and trigger phrases associated with the template and one or more of the sections. In this way, the doctor merely needs to mention the trigger phrases during the doctor's conversation with the patient and the AI automatically identifies the appropriate template based on a particular trigger phrase and fill in the appropriate sections based on the trigger phrases, thereby significantly reducing the time the doctor takes to fill in a patient visit note because the AI is able to complete most (e.g., >80%) of the patient visit note based on the conversation between the doctor and the patient.

Figure 5:
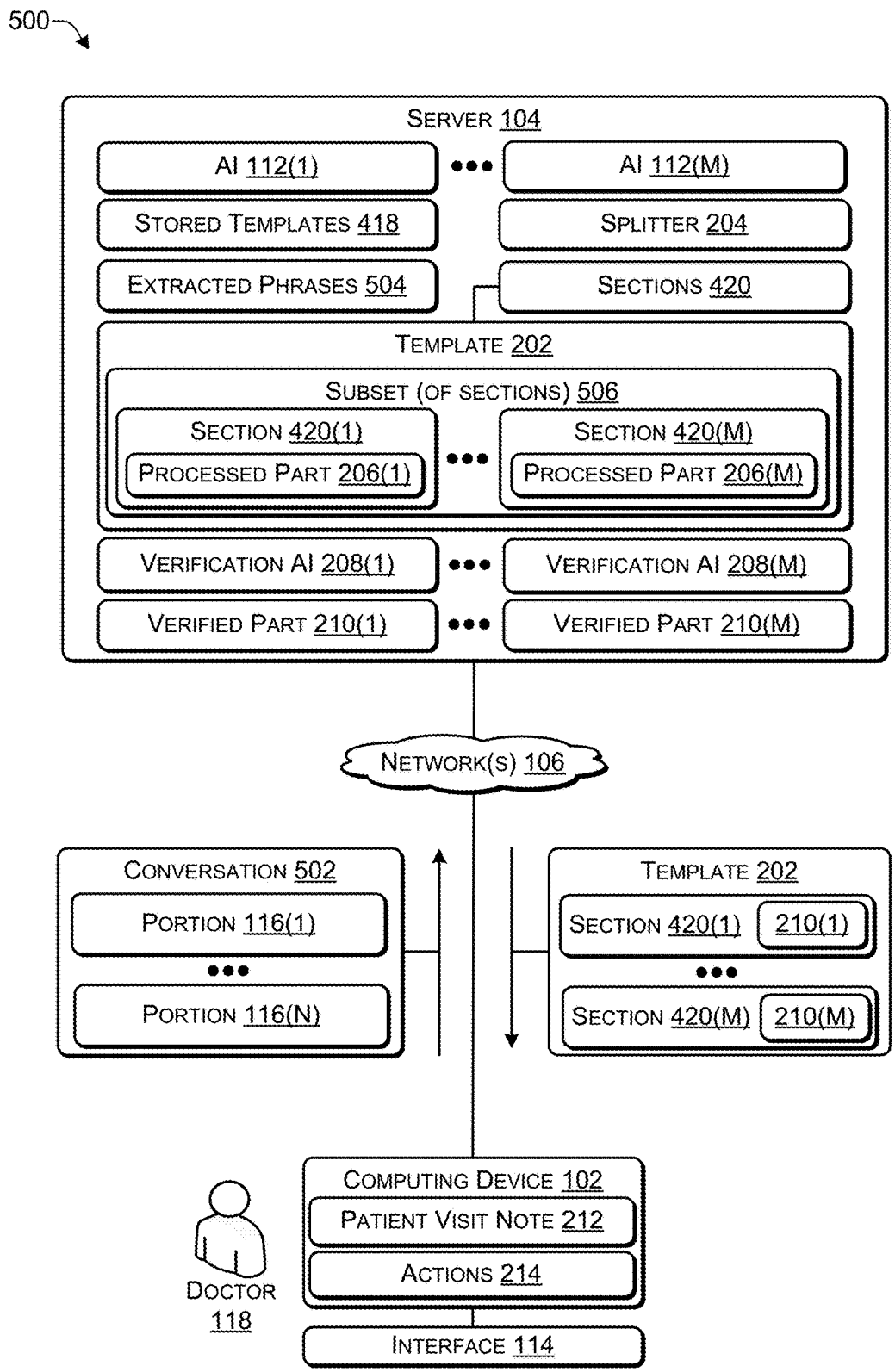
FIG. 5 is a block diagram of a system to create a patient visit note using an artificial intelligence (AI) based on a conversation between a doctor and a patient, according to some implementations.

FIG. 5 is a block diagram of a system 500 to create a patient visit note using an artificial intelligence (AI) based on a conversation between a doctor and a patient, according to some implementations. After the AI 112 determines that the doctor 118 has completed the conversation 502 (either in-person or via an audio or video call) with the patient, the AI 112 performs an analysis of the conversation 502. The conversation 502 includes the multiple portions 116(1) to 116(N). The conversation 502 may include audio data of the conversation between the doctor 118 and the patient 120, a text-based transcript, or a combination of both.

The AI 112 extracts one or more phrases from the conversation 502 to create extracted phrases 504. The AI 112 identifies trigger phrases among the extracted phrases 504. For example, a particular phrase that includes a particular diagnoses may cause the AI 112 to select a particular template 202 from the stored templates 418. The AI 112 may use one or more of the extracted phrases 504 to populate the template 202 with a subset 506 of the sections 420 that were identified from the training data 402. Thus, in some cases, the template 202 may be created (customized) on the fly by the AI 112 based on the extracted phrases 504 from the conversation 502. This further saves the doctor 118 time because the AI 112 is able to create the custom template 202 from analyzing the conversation 502 and without the doctor 118 specifying the sections 420 to be used in the template 202. Instead, the AI 112 determines the sections 420 of the template 202 based on the extracted phrases 504 from the conversation 502.

To expedite creation of the patient visit note 212, multiple instances of the AI 112, such as AI 112(1) to AI 112(M) (M>0), may be used to populate each of the sections 420(1) to 420(M) of the subset 506. For example, the AI 112(1) may be used to populate the section 420(1) with the processed part 206(1) of the conversation 502 and the AI 112(1) may be used to populate the section 420(M) with the processed part 206(M) of the conversation 502.

To improve an accuracy of the processed parts 206 of the sections 420, multiple verification AI's, verification AI 208(1) to 208(M), may be used to verify individual ones of the processed parts 206 to create the verified parts 210. For example, the verification AI 208(1) may verify the processed part 206(1) to create the verified parts 210(1) and the verification AI 208(M) may verify the processed part 206(M) to create the verified parts 210(M).

The server 104 provides the template 202 with the sections 420(1) to 420(M) filled in with the verified parts 210(1) to 210(M), respectively, to the computing device 102 as the patient visit note 212. The doctor 118 is able to view the patient visit note 212 and make any desired modifications.

The AI 112 receives the conversation 502 that includes the portions 116(1) to 116(N). The conversation 502 may be in the form of audio data captured by a microphone, text data created by transcribing the audio data of the conversation, or a combination of both. For example, if the audio data does not yield a word or phrase that can be accurately transcribed, the audio data may be preserved for analysis by the AI 112.

After receiving the conversation 502, the AI 112 may extract one or more phrases to create extracted phrases 504. The AI 112 may use the extracted phrases 504 to select a particular template from the stored templates 418 to create the selected template 202. The AI 112 may use the conversation 502 to populate the selected template 202 to create the patient visit note 212. The AI 112 may use the extracted phrases 504 as trigger phrases to identify a subset of sections 506 (from the available sections 420), such as sections 420(1) to 420(M) (V<=M<0). Multiple instances of the AI 112 (e.g., AI 112(1) to AI 112(M)) may populate, in parallel, individual sections 420(1) to 420(M) with the processed parts 206 of the conversation 502. By populating the sections 420 in parallel, latency is reduced and the patient visit note 212 is produced quickly. Multiple verification AI 208(1) to 208(M) verify each of the processed parts 206(1) to 206(M) in parallel to create the verified parts 210(1) to 210(M), respectively.

Thus, an AI may receive a conversation between a doctor and a patient (e.g., in the form of a text-based transcript). The AI determines a template (for a patient visit note) and a layout of the template based on an analysis of the conversation. For example, the AI may use one or more phrases in the conversation to determine the template and to determine the sections (and an order of the sections). The AI outputs a patient visit note by inserting information from the conversation into the appropriate places in the sections of the template. The template is thus populated based on trigger phrases from the conversation. Each section is processed in parallel and verified in parallel to reduce the time to create the patient visit note. This saves the doctor a significant amount of time because the patient visit note is populated based on the conversation between the doctor and patient and the information is verified prior to sending the patient visit note to the doctor.

In the flow diagram of FIGS. 6, 7, 8, 9, 10, and 11, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, modules, components, data structures, and the like that perform particular functions or implement particular abstract data types. The order in which the blocks are described is not intended to be construed as a limitation, and any number of the described operations can be combined in any order and/or in parallel to implement the processes. For discussion purposes, the processes 600, 700, 800, 900, 1000, and 1100 are described with reference to FIGS. 1, 2, 3, 4, and 5 as described above, although other models, frameworks, systems and environments may be used to implement these processes.

Figure 6:
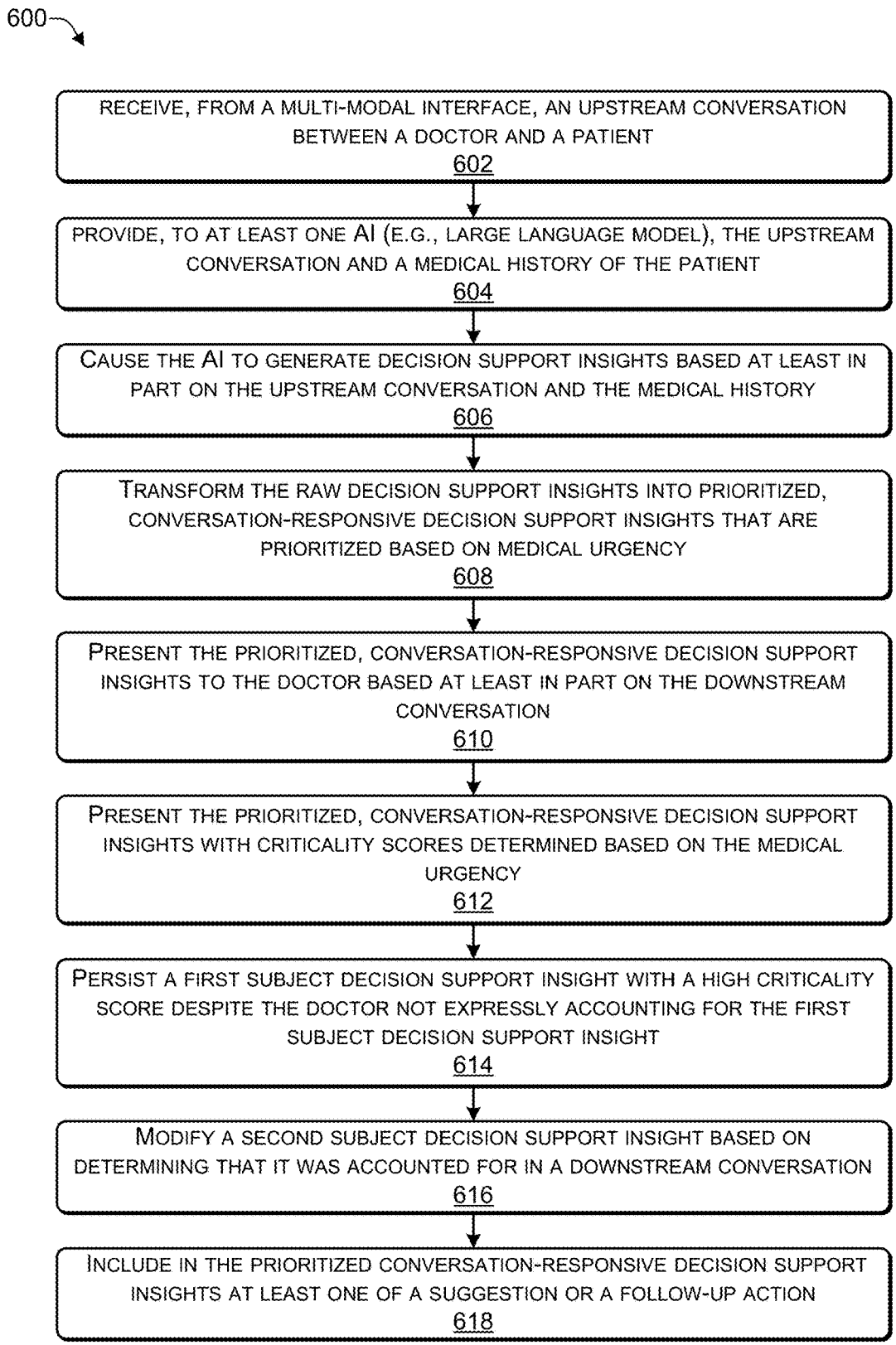
FIG. 6 is a flowchart of a process that includes causing an artificial intelligence (AI) to generate decision support insights, according to some implementations.

FIG. 6 is a flowchart of a process 600 that includes causing an artificial intelligence (AI) to generate decision support insights, according to some implementations. The process 600 may be performed by one or more components of the server 104 and/or the computing device 102 of FIGS. 1, 2, 3, 4, and 5.

At 602, the process may receive, from a multimodal interface, an upstream conversation between a doctor and a patient. For example, in FIG. 1, the AI 112 may receive, from the interface 114, the portion 116(1) of the upstream conversation between the doctor 118 and the patient 120.

At 604, the process may provide, to at least one AI (such as a large language model), the upstream conversation and a medical history of the patient. At 606, the process may cause the AI to generate decision support insights based at least in part on the upstream conversation and the medical history. For example, in FIG. 1, AI 112 (e.g., a large language model) may receive the upstream portion 116(1) of the conversation and access a medical history of the patient using the EMR 108. The AI 112 may generate decision support insights 140 based at least in part on the upstream portion 116(1) of the conversation and the medical history from the EMR 108.

At 608, the process may transform the raw decision support insights into prioritized conversation responsive decision support insights that are prioritized based on medical urgency. At 610, the process may present the prioritized, conversation responsive decision support insights to the doctor based at least in part on the downstream conversation. At 612, the process may present individual ones of the prioritized, conversation responsive decision support insights with an associated criticality score that is determined based on the medical urgency. For example, in FIG. 1, the post processing 128 (located either at the computing device 102 or at the server 104) may transform the output 126(N) (e.g., raw decision support insights) into prioritized conversation responsive decision support insights 140 that are prioritized (by the prioritization module 134) based on medical urgency. The prioritized, conversation responsive decision support insights 140(N) are presented to the doctor 118 based at least in part on the downstream portion 116(N) of the conversation. Individual prioritized, conversation responsive decision support insights 140(N) may be presented by the computing device 102 with an associated criticality score that is determined based on the medical urgency.

At 614, the process may persist a first subject decision support insight with a high criticality score despite the doctor not expressly accounting for the first subject decision support insight. For example, in FIG. 3, the decision support insights 140(2) may include an insight with a high criticality score. If the AI 112 determines, based at least in part on the portion 116(2) of the conversation, that the doctor has not expressly accounted for the insight with the high criticality score, the AI 112 may persist the insight with the high criticality score in one or more subsequent decision support insights 140(N), e.g., until the doctor expressly accounts for the insight with the high criticality score.

At 616, the process may modify a second subject decision support insight based on determining that it was accounted for in the downstream conversation. For example, in FIG. 1, the AI 112 may include an instruction in the adjustments 132 to modify a second subject decision support insight in the decision support insights 140 based on determining that it was accounted for in the downstream portion 116(N) of the conversation. To illustrate, the AI 112 may determine that one of the suggestions 138 to ask the patient a particular question can be removed because either the doctor 118 asked the question or the patient 120 volunteered information answering the question. To illustrate, if the doctor 118 determines that the patient 120 is likely suffering from high blood pressure and is considering prescribing a diuretic, the AI 112 may provide in the suggestions 138 that the doctor 118 ask the patient 120 if the patient has previously suffered from gout. Before or while the suggestions 138 are being displayed by the computing device 102, the doctor 118 may ask the patient 120 whether the patient 120 has previously suffered from gout. Alternately, before or while the suggestions 138 are being displayed by the computing device 102, the patient 120 may volunteer that the patient 120 has previously suffered from gout. In either case, the AI 112 determines that the suggestion to the doctor 118 to ask the patient 120 the question (whether the patient 120 has previously suffered from gout) is no longer applicable and includes an instruction in the adjustments 132 to remove that particular question from the suggestions 138 or the decision support insights 140(N).

At 618, the process may include in the prioritized conversation responsive decision support insights at least one of a suggestion or a follow-up action. For example, in FIG. 1, the suggestions 138 in the decision support insights 140(N) may include questions for the doctor 118 to ask the patient 120, suggestions for one or more tests for the patient 120, suggestions for one or more referrals, suggested diagnoses, suggested prescriptions, and other insights derived from the portion 116 of the conversation, the EMR 108, and the medical knowledge databases 110.

Thus, an AI may receive a portion of a conversation between a doctor and a patient and generate one or more decision support insights based on the portion of the conversation and a medical history of the patient. The rod this decision support insights may be prioritized based on medical urgency and presented accordingly. For example, urgent decision support insights may be presented in a larger font, in a different font, in a bolder font, in a different colored font, or the like to enable the doctor to easily identify the more critical insights from other insights. The AI may persist, in a subsequent set of decision support insights, a critical insight that the doctor does not expressly account for. If the AI determines that a particular issue identified in an insight has either been raised by the doctor or addressed by the patient, then the AI may modify the insight to indicate that it has been accounted for. The decision support insights may include a suggestion or a follow-up action. In this way, the AI is able to augment the doctor's insights by suggesting alternatives that the doctor may not normally consider and reminding the doctor of insights that normally occur to the doctor. Thus, even if the doctor forgets to ask a question or perform an action that the doctor normally does, the AI is able to remind the doctor of the question or action to be performed.

Figure 7:
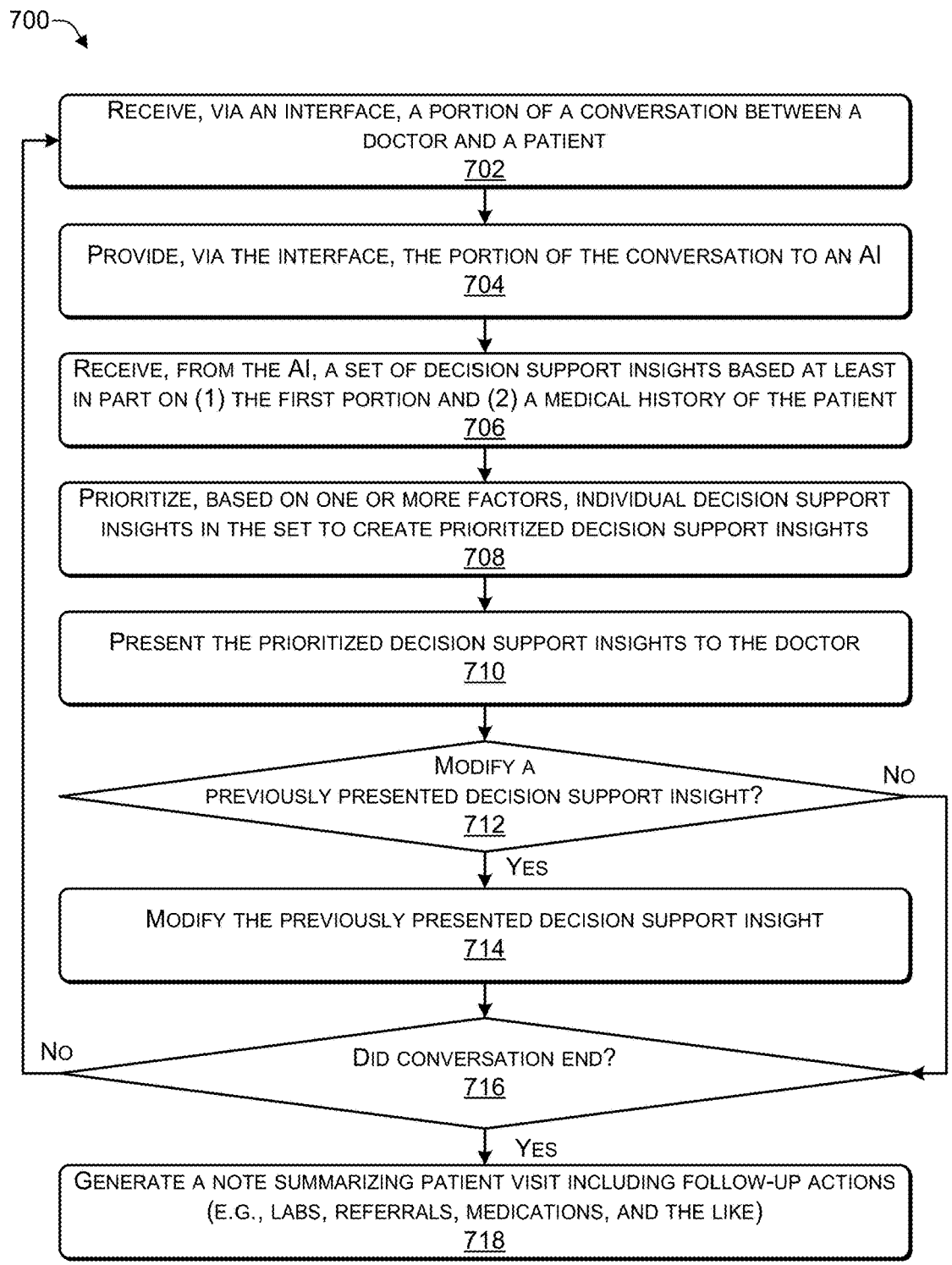
FIG. 7 is a flowchart of a process that includes presenting prioritized decision support insights to a doctor, according to some implementations.

FIG. 7 is a flowchart of a process 700 that includes presenting prioritized decision support insights to a doctor, according to some implementations. The process 700 may be performed by the interface 114 or one or more components of the computing device 102 of FIGS. 1, 2, 3, 4, and 5.

At 702, the process may receive, via an interface, a portion of a conversation between a doctor and a patient. At 704, the process may provide, via the interface, the portion of the conversation to an AI. For example, in FIG. 1, the interface 114 may receive the portion 116(1) of the conversation between the doctor 118 and the patient 120. The interface 114 may provide the portion 116(1) of the conversation, as audio data, transcribed text data, or a combination of both, to the server 104 for the AI 112 to process. For example, if portions of the audio data could not be transcribed with a particular degree of confidence (e.g., 90%, 95% or the like), then audio data may be included with a transcription of the audio data.

At 706, the process may receive, from the AI, a set of decision support insights based at least part on the first portion of the conversation and a medical history of the patient. At 708, the process may prioritize, based on one or more factors, individual decision support insights in the set of decision-support insights to create prioritized decision support insights. At 710, the process may present the prioritized decision support insights to the doctor. For example, in FIG. 1, the computing device 102 may receive the output 126 from the server 104 that the AI 112 has determined based on the portion 116(1) of the conversation and a medical history of the patient 120 derived from the electronic medical records 108. The computing device 102 may perform post processing 128 of the output 126(N), including prioritizing the decision support insights 140(N), based on one or more factors, such as based on a criticality score. In some cases, the criticality score may be determined based on medical urgency.

At 712, the process may determine whether to modify a previously presented decision-support insight. If the process determines, at 712, that "yes" a previously presented decision-support insight is to be modified, then the process may proceed to 714, where the previously presented decision-support insight is modified, and the process proceeds to 716. If the process determines, at 712, that "no" the previously presented decision-support insight is not to be modified, then the process proceeds to 716. For example, in FIG. 1, the post processing 128 may determine whether a previously presented decision-support insight (of the insights 140) is to be modified. For example, the adjustments 132 may include instructions on whether to modify one or more of the decision support insights 140(N). To illustrate, if the doctor has not expressly acknowledged an important or critical decision support insight, then the adjustments 132 may include displaying the decision-support insight in such a way as to indicate the importance or criticality of the insight. As another illustration, if a decision support insight was to obtain particular information from the patient 120 and either the doctor 118 asked a question to obtain the particular information or the patient 120 volunteered the particular information, then the adjustments 132 may include an instruction to remove the decision-support insight to obtain the particular information from the displayed decision support insights 140. If the adjustments 132 is an empty set and there are no instructions to make adjustments, then no adjustments are made to the decision support insights 140 (N).

At 716, the process determines whether the conversation has ended. If the process determines, at 716, that "no" the conversation has not ended, then the process proceeds back to 702 to receive a subsequent portion of the conversation between the doctor and the patient via the interface. For example, in FIG. 3, the interface 114 may determine whether the conversation between the doctor 118 and the patient 120 has ended. If a determination is made that the conversation has not ended, then the interface 114 may receive a subsequent portion 116 of the conversation between the doctor 118 and the patient 120.

If the process determines, at 716, that "yes" the conversation has ended, then the process generates a note summarizing the patient visit, including follow-up actions (e.g., labs, referrals, medications, and the like), at 718. For example, in FIG. 2, if a determination is made that the conversation between the doctor 118 and the patient 120 has ended, then the process generates patient visit note 212 summarizing the patient visit and suggested follow-up actions 214 (e.g., labs, referrals, medications, and the like).

Thus, a portion of a conversation (e.g., that includes one or more turns) is captured by an interface and sent to an AI hosted by a server. The conversation may be sent as audio data, as transcribed text data, or a combination of both. The AI may access the patient's medical records and in some cases, access current medical knowledge databases, to generate decision support insights for the doctor. The decision support insights may be prioritized prior to being presented to the doctor. For example, the decision-support insight may be prioritized based on medical urgency relative to the patient or another factor. In some cases, the AI may provide instructions to modify a previously presented decision-support insight by persisting an insight that the doctor has not expressly acknowledged or by modifying or removing an insight associated with particular information. For example, if the AI has made a suggestion to the doctor to request particular information from the patient and the doctor has either asked for the particular information or the patient has volunteered the particular information, then the AI may remove the suggestion from the decision support insights. If the AI has made a suggestion to the doctor to request particular information from the patient and part of the particular information has been obtained, then the AI may modify the suggestion to obtain the remaining portion of the particular information.

Figure 8:
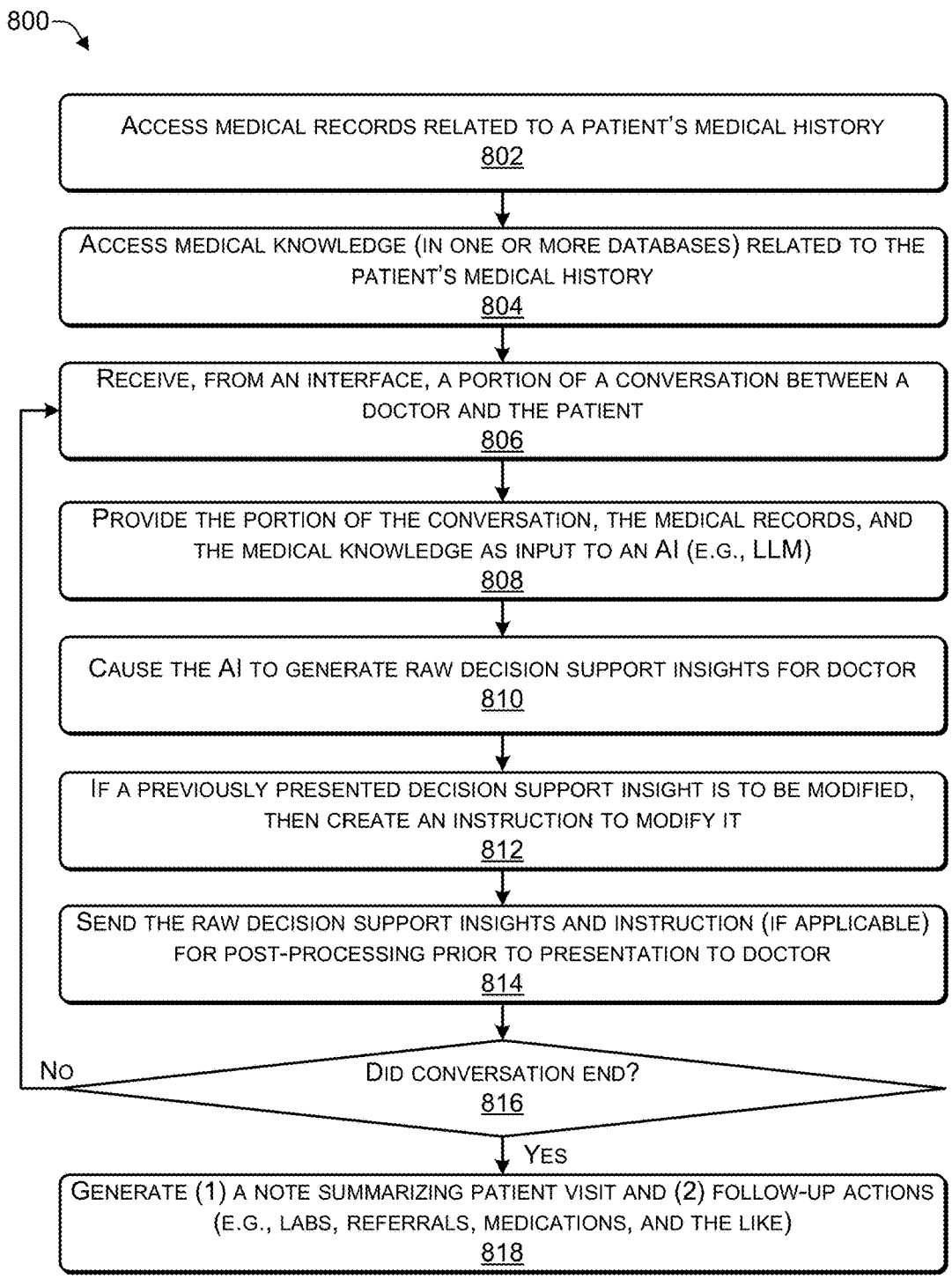
FIG. 8 is a flowchart of a process that includes sending raw decision support insights to an interface for post-processing prior to presentation to a doctor, according to some implementations.

FIG. 8 is a flowchart of a process 800 that includes sending raw decision support insights to an interface for post-processing prior to presentation to a doctor, according to some implementations. The process 800 may be performed by one or more components of the server 104 of FIGS. 1, 2, 3, 4, and 5.

At 802, the process may access medical records related to a patient's medical history. At 804, the process may access medical knowledge (in one or more databases) related to the patient's medical history. At 806, the process may receive, from an interface, a portion of a conversation between a doctor and the patient. At 808, the process may provide the portion of the conversation, the medical records, and the medical knowledge as input to an AI (e.g., LLM). At 810, the process may cause the AI to generate raw decision support insights for the doctor. At 812, if a previously presented decision-support insight is to be modified in the process creates an instruction to modify it. At 814, the process sends the raw decision support insights and instruction (if applicable) to the interface for postprocessing prior to presentation to a doctor. For example, in FIG. 1, the orchestrator 111 may access electronic medical records 108 related to a medical history of the patient 120. The orchestrator 111 may access medical knowledge (in one or more databases 110) related to the patient's medical history. The orchestrator 111 may receive the portion 116(1) of a conversation between the doctor 118 and the patient 120 as audio data, transcribed text data, or a combination of both. The orchestrator 111 may provide the portion 116(1) of the conversation, the relevant medical records 108, and the relevant medical knowledge 110 as input to the AI 112 (e.g., LLM). The AI 112 may generate raw decision support insights in the output 126(N) that are processed and then presented to the doctor 118. For example, the output 126(N) of the AI 112 may be processed using a post processing module 128. While the post processing module 128 is illustrated as being executed by the computing device 102, in some cases, the post processing module 128 may be executed by the server 104 and the processed decision support insights sent as the output 126 (N) to the computing device 102. If a previously presented decision-support insight is to be modified (e.g., persist an unacknowledged insight or modify an insight that has been partially or fully responded to by either the doctor or the patient), then the AI 112 creates an adjustment instruction in the adjustments 132 modify one of the insights.

At 816, the process determines whether the conversation has ended. If the process determines, at 816, that "no" the conversation has not ended, then the process proceeds back to 806 to receive a subsequent portion of a conversation between the doctor and the patient from the interface. If the process determines, at 816 that "yes" the conversation has ended, then the process generates: (1) a note summarizing the patient visit and (2) follow-up actions. For example, in FIG. 3, the process determines whether the conversation between the doctor 118 and the patient 120 has ended. If the process determines, that the conversation has not ended, then the process proceeds to receive a subsequent portion 116 of a conversation between the doctor 118 and the patient 120. If the process determines, that the conversation between the doctor 118 and the patient 120 has ended, then the process generates: (1) the patient visit note 212 summarizing the patient visit and (2) the follow-up actions 214.

Thus, an orchestrator may determine that a patient is about to visit a doctor and access medical records related to the patient's medical history. The orchestrator may access medical knowledge related to the patient's medical history. The orchestrator may receive a portion of a conversation between a doctor and a patient in the form of audio data, transcribed text data, or a combination of both. The orchestrator may provide the portion of the conversation along with the patient's medical history and the medical knowledge relevant to the patient's medical history to an AI. The AI may generate raw decision support insights designed to support the doctor. If a previously presented decision-support insight is to be modified then the AI may create an instruction to modify the previously presented decision-support insight. The raw decision support insights and instruction, if applicable, may be sent for post processing prior to presentation to the doctor. The post processing of the raw decision support insights may occur at a server (e.g., where the AI is executing) or at the computing device associated with the doctor. After determining that the conversation between the doctor and patient has ended the process may generate a note summarizing the patient visit and follow-up actions, such as labs, referrals, medications, and the like to enable the doctor to quickly perform the follow-up actions.

Figure 9:
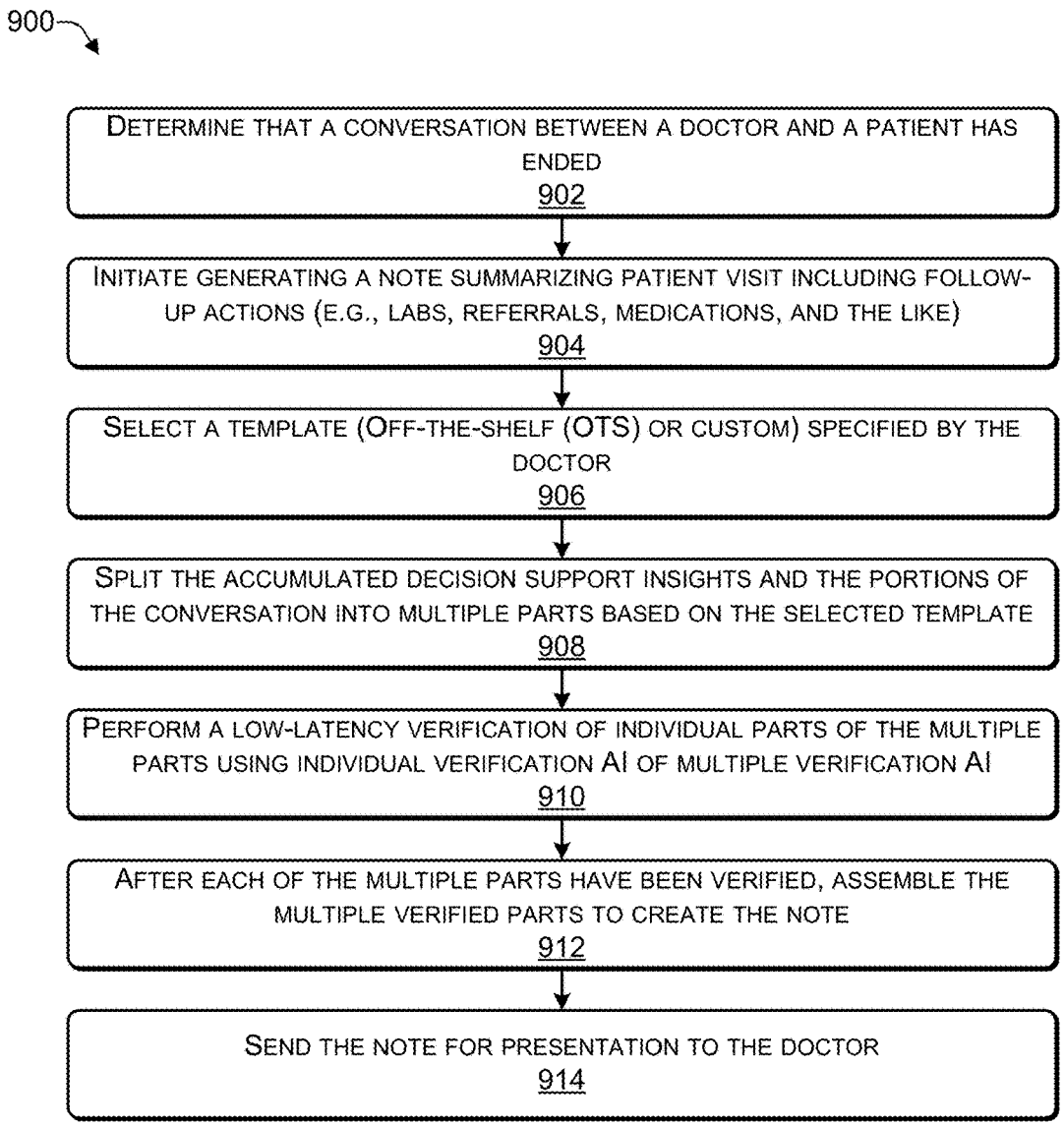
FIG. 9 is a flowchart of a process that includes sending a note to an interface for presentation to a doctor, according to some implementations.

FIG. 9 is a flowchart of a process 900 that includes sending a note to an interface for presentation to a doctor, according to some implementations. The process 900 may be performed by one or more components of the server 104 of FIGS. 1, 2, 3, 4, and 5.

At 902, the process may determine that a conversation between a doctor and a patient has ended. At 904, the process may initiate generating a note summarizing the patient visit including follow-up actions, e.g., labs, referrals, medications, and the like). For example, in FIG. 2, after determining that the conversation between the doctor 118 and the patient 118 (of FIG. 1) has ended, the orchestrator 111 or the interface 110 may instruct the AI 112 to generate the patient visit note 212 and the actions 214.

At 906, the process may select a template that is either an off-the-shelf (OTS) template or a custom template specified by the doctor. At 908, the process may split the accumulated decision support insights and the portions of the conversation into multiple parts based on the selected template. At 910, the process may perform a low latency verification of individual parts of the multiple parts using individual verification AIS of multiple verification AI. For example, in FIG. 2, the splitter 204 may split the portions 116 and the decision support insights 112, based on the template 202, to create the processed parts 206. Individual verification AIs of the multiple verification AIs 208 may verify individual parts of the processed parts 206 to create the verified parts 210. Each verification AI 208 may be trained to verify a particular section 420. For example, the verification AI 208(M) may be trained to verify the section 420(M), for each M.

At 912, after each of the multiple parts have been verified, the process may assemble the multiple verified parts to create the note. At 914, the note may be sent for presentation to the doctor. For example, the verified parts 210 may be sent from the server 104 to the computing device 102 and assembled to create the patient visit note 212 including the actions 214.

Thus, after a conversation between a doctor and a patient has concluded, an AI may use a template to split up the accumulated conversation and, in some cases, the accumulated decision support insights to create multiple parts. Individual parts of the multiple parts may be verified by individual verification AIs that verify the content of each part of the note based on the relevant portions of the conversation and/or relevant portions of the decision support insights. The verified parts are assembled, based on the template, to create the patient visit note that summarizes the patient's visit. The note may include one or more follow-up actions that the doctor can select to be performed. In this way, the doctor is spared from spending time entering notes and entering and initiating various follow-up actions. This saves the doctor time and allows the doctor to perform tasks, such as seeing more patients, rather than spending time doing paperwork.

Figure 10:
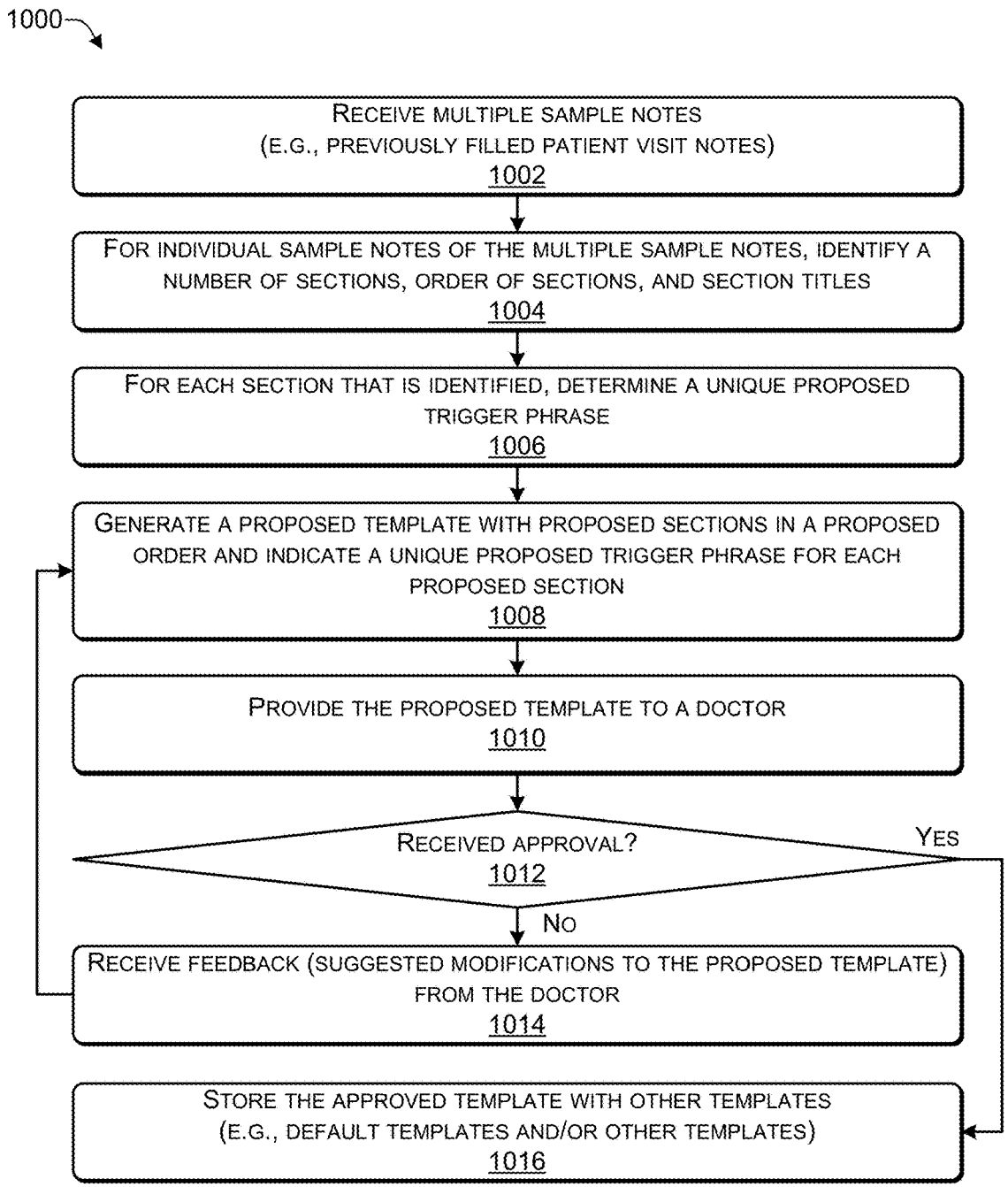
FIG. 10 is a flowchart of a process that includes creating a proposed template based on an analysis of multiple sample notes, according to some implementations.

FIG. 10 is a flowchart of a process 1000 that includes creating a proposed template based on an analysis of multiple sample notes, according to some implementations. The process 1000 may be performed by the server 104 of FIGS. 1, 2, 3, 4 and 5.

At 1002, the process may receive multiple sample notes (e.g., prefilled patient visit notes). For example, in FIG. 4, the server 104 may receive the training data 402 that includes multiple sample notes 404, e.g., previously completed patient visit notes, having a style that the doctor 118 desires to use to create a template.

At 1004, for individual sample notes of the multiple sample notes, the process may identify a number of sections, an order of the sections, and section titles. At 1006, for each section that is identified, the process may determine a unique proposed trigger phrase. At 1008, the process may generate a proposed template with proposed sections and a proposed order and indicate a unique proposed trigger phrase for each proposed section. At 1010, the process may provide the proposed template to a doctor (e.g., for review). For example, in FIG. 4, the AI 112 identifies the sections 406 in each of the sample notes 404, determines how many of the sections 406 are included in each of the sample notes 404, determines an order of the sections 406 in each of the sample notes 404, a section title associated with each of the sections 406, and determines a unique trigger phrase for at least some of the sections 406. For each section 406 that the AI 112 identifies as being unique, the AI 112 may determine a unique trigger phrase to associate with that section. The server 104 may provide the proposal 408 including the proposed template 410 with the proposed sections 412, associated trigger phrases 414, and the proposed section order 416, to the computing device 102.

At 1012, the process may determine whether the proposed template has received approval from the doctor. If the process determines, at 1012 that "no" the proposed template has not received approval from the doctor, then the process may proceed to 1014, where the process receives feedback (suggested modifications to the proposed template) from the doctor. If the process determines, at 1012, that "yes" the proposed template has received approval from the doctor, then, at 1016, the process stores the approved template with other templates (e.g. such as default templates and/or other templates). For example, in FIG. 4, after the doctor 118 reviews the proposal 408, the doctor 118 may use a computing device 102 to provide the feedback 418 to the server 104. The server 104 may receive the feedback 418. If the feedback 418 includes suggested modifications to the proposed template 410, then the server 104 may modify the proposed template 410 based on the feedback 418 and provide a revised proposed template 410. If the feedback 418 includes approval of the proposed template 410 from the doctor 118, then the server 104 may store the proposed template 410 with the stored templates 418.

Thus, a doctor may provide sample notes (previously created patient visit notes) which the AI analyzes and uses to create a proposed template. Some sections of the template may be relatively generic while other sections may be specific to particular conditions. The AI may determine a unique trigger phrase to associate with each template and with unique sections. The AI may propose which trigger phrase is associated with which template and with which section and the doctor may modify or confirm the trigger phrases. The AI may extract sections from multiple sample notes and determine an order of the sections in the note. The AI provides the proposed patient visit note structure (proposed template) to the doctor for review. The doctor may modify the proposed patient visit note structure by modifying one or more of the name of the template, name of individual sections, the number of sections, the section order, and trigger phrase associated with each section, and so on. In some cases, the doctor may modify the proposed template using voice commands that direct the AI to modify the proposed template. The AI receives the feedback from the doctor, modifies the proposed template, provides the modified proposed template to the doctor for review until the doctor indicates, in the feedback, that the doctor has approved the proposed template. In this way, the doctor merely needs to mention the trigger phrases during the doctor's conversation with the patient and the AI automatically identifies the appropriate template based on a particular trigger phrase and fills in the appropriate sections based on the trigger phrases. The time the doctor takes to fill in a patient visit note is significantly reduced because the AI is able to complete most (e.g., >80%) of the patient visit note based on the conversation between the doctor and the patient.

Figure 11:
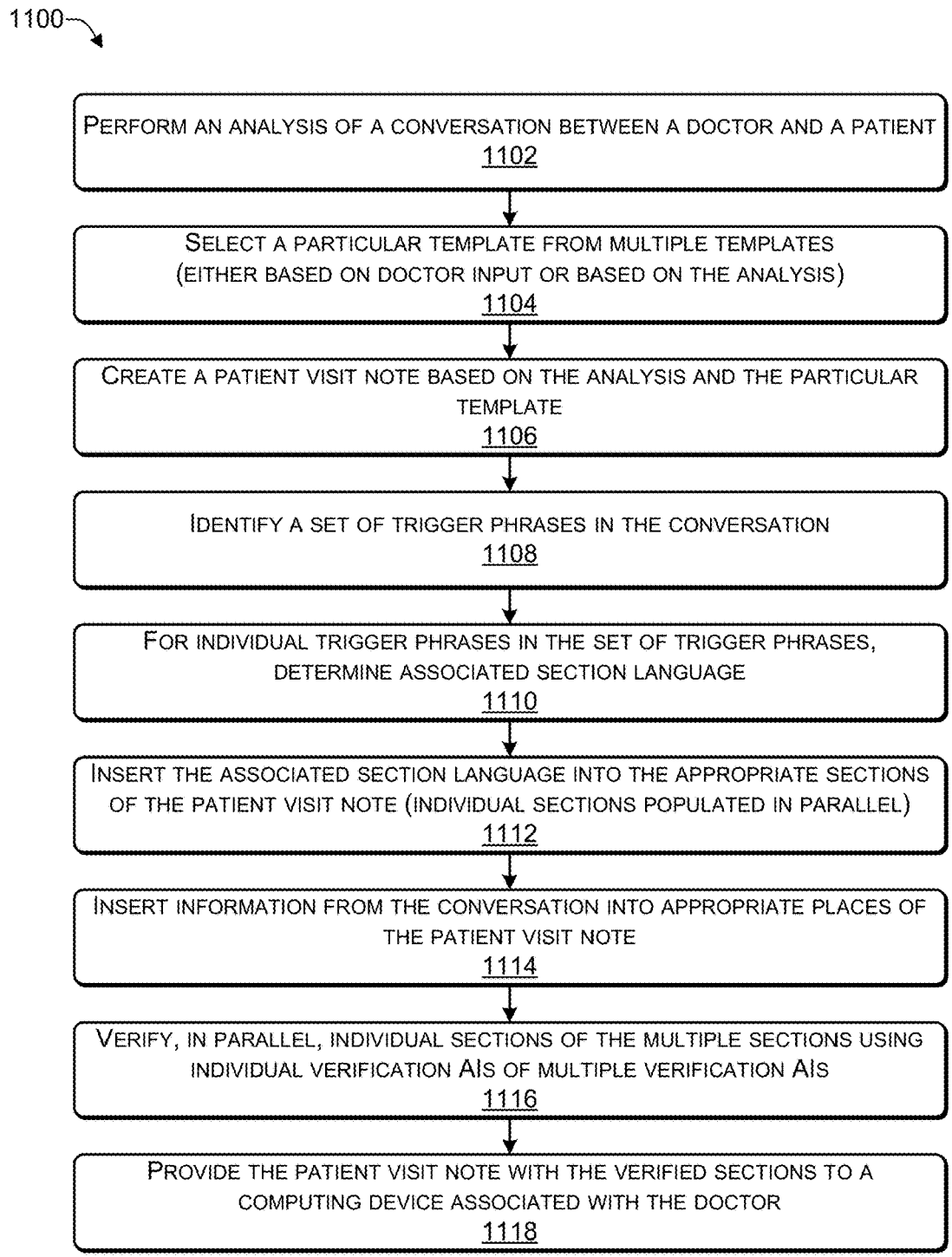
FIG. 11 is a flowchart of a process that includes creating and verifying sections of a template to create a patient visit note, according to some implementations.

FIG. 11 is a flowchart of a process 1100 that includes creating and verifying sections of a template to create a patient visit note, according to some implementations. The process 1100 may be performed by the server 104 of FIGS. 1, 2, 3, 4 and 5.

At 1102, the process may perform an analysis of a conversation between a doctor and a patient. At 1104, the process may select a particular template from multiple templates, either based on doctor input or based on the analysis (e.g., based on identifying a trigger phrase associated with the particular template in the conversation). At 1106, the process may create a patient visit note based on the analysis and the particular template. At 1108, the process may identify a set of trigger phrases in the conversation. At 1110, for individual trigger phrases in the set of trigger phrases, the process may determine associated section language. At 1112, the process may insert the associated section language into the appropriate sections of the patient visit note. The individual sections may be populated in parallel using multiple instances of the AI. At 1114, the process may insert information from the conversation into appropriate places (e.g., appropriate sections) of the patient visit note. At 1116, the process may verify, in parallel, individual sections of the multiple sections using individual verification AIs of multiple verification AIs. At 1118, the process may provide the patient visit note with the verified sections to a computing device associated with the doctor.

For example, in FIG. 5, the AI 112 may perform an analysis of the conversation 502 (between the doctor 118 and the patient 120 of FIGS. 1, 2, and 3). The AI 112 may select a particular template 202 from multiple stored templates 418, either based on doctor input or based on the analysis (e.g., based on identifying a trigger phrase associated with the particular template 202 in the conversation 502). The AI 112 may create the patient visit note 212 based on the analysis and the particular template 202. For example, the AI 112 may identify a set of phrases 504 in the conversation. For individual trigger phrases in the extracted phrases 504, the AI 112 may determine associated section language (e.g., treatment plan, prescription, or the like) and insert the associated section language into the appropriate sections of the patient visit note 212. The individual sections 420 may be populated in parallel using multiple instances of the AI 112(1) to 112(M). Each instance of the AI 112 may insert information from the conversation 502 into appropriate places (e.g., appropriate sections 402) of the patient visit note 212. The individual verification AIs 208 may verify, in parallel, individual sections 420. The server 104 process may provide the patient visit note 212 with the verified sections 420 (and verified parts 210) to the computing device 118 associated with the doctor 118.

Thus, an AI may receive a conversation between a doctor and a patient (e.g., in the form of a text-based transcript). The AI may automatically (without human interaction) determine a template (for a patient visit note) and a layout of the template based on an analysis of the conversation. For example, the AI may use one or more phrases in the conversation to determine the template and to determine the sections (and an order of the sections). The AI outputs a patient visit note by inserting information from the conversation into the appropriate places in the sections of the template. The template may be populated based on trigger phrases from the conversation and portions of the conversation. Each section is processed in parallel and verified in parallel to reduce the time to create the patient visit note. This saves the doctor a significant amount of time because the patient visit note is automatically populated based on the conversation between the doctor and patient.

Figure 12:
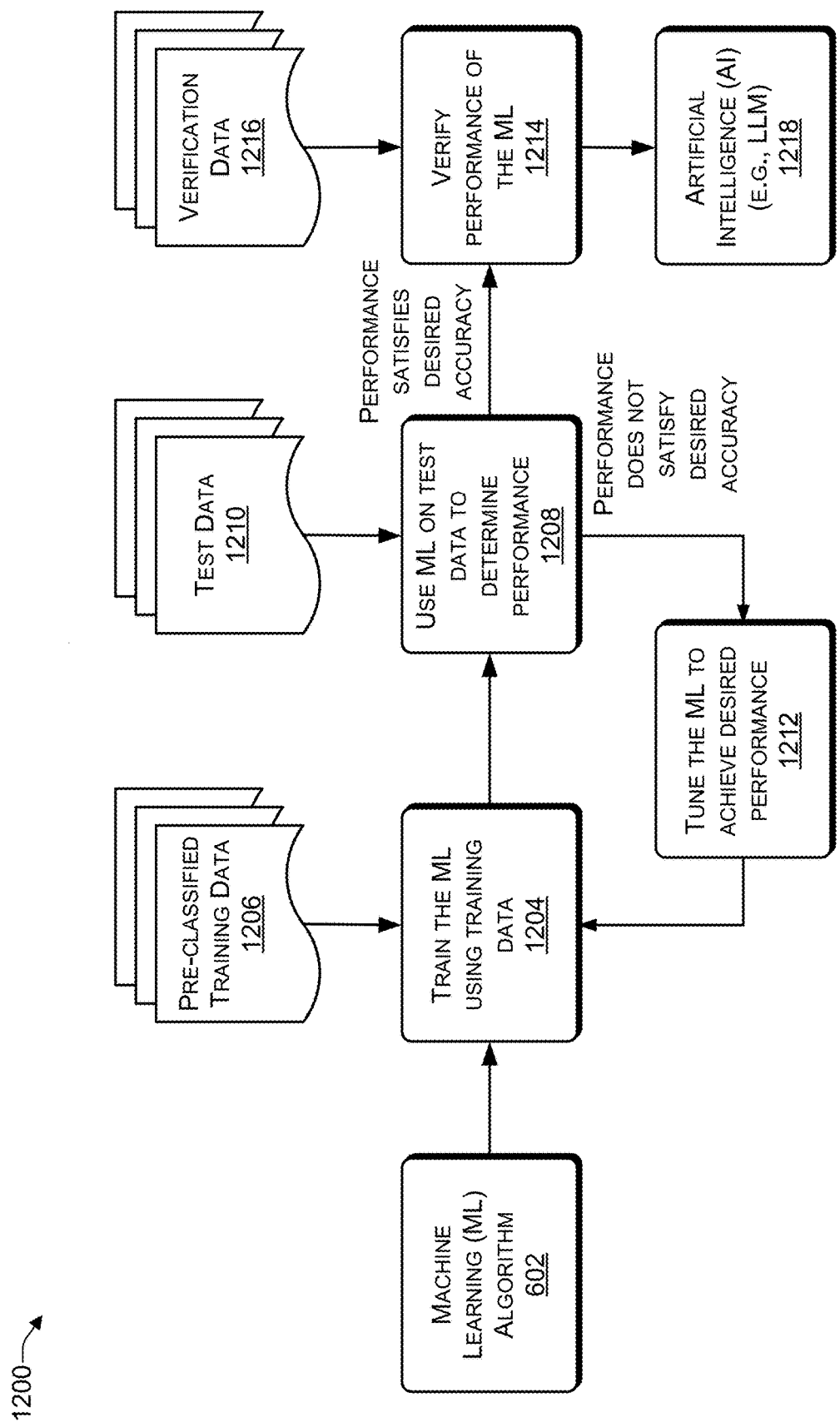
FIG. 12 is a flowchart of a process to train a machine learning algorithm, according to some implementations.

FIG. 12 is a flowchart of a process 1200 to train a machine learning algorithm, according to some implementations. For example, the process 1200 may be performed to create the one or more of the AIs 112 and the multiple verification AIs 108.

At 1202, a machine learning algorithm (e.g., software code) may be created by one or more software designers. At 1204, the machine learning algorithm may be trained using pre-classified training data 1206. For example, the training data 1206 may have been pre-classified by humans, by machine learning, or a combination of both. After the machine learning has been trained using the pre-classified training data 1206, the machine learning may be tested, at 1208, using test data 1210 to determine a performance metric of the machine learning. The performance metric may include, for example, precision, recall, Frechet Inception Distance (FID), or a more complex performance metric. For example, in the case of a classifier, the accuracy of the classification may be determined using the test data 1210.

If the performance metric of the machine learning does not satisfy a desired measurement (e.g., 95%, 98%, 99% in the case of accuracy), at 1208, then the machine learning code may be tuned, at 1212, to achieve the desired performance measurement. For example, at 1212, the software designers may modify the machine learning software code to improve the performance of the machine learning algorithm. After the machine learning has been tuned, at 1212, the machine learning may be retrained, at 1204, using the pre-classified training data 1206. In this way, 1204, 1208, 1212 may be repeated until the performance of the machine learning is able to satisfy the desired performance metric.

For example, in the case of a classifier, the classifier may be tuned to be able to classify the test data 1210 with the desired accuracy.

After determining, at 1208, that the performance of the machine learning satisfies the desired performance metric, the process may proceed to 1214, where verification data 1216 may be used to verify the performance of the machine learning. After the performance of the machine learning is verified, at 1214, the machine learning 1202, which has been trained to provide a particular level of performance may be used as the artificial intelligence (AI) 112 or the verification AIs 108.

Figure 13:
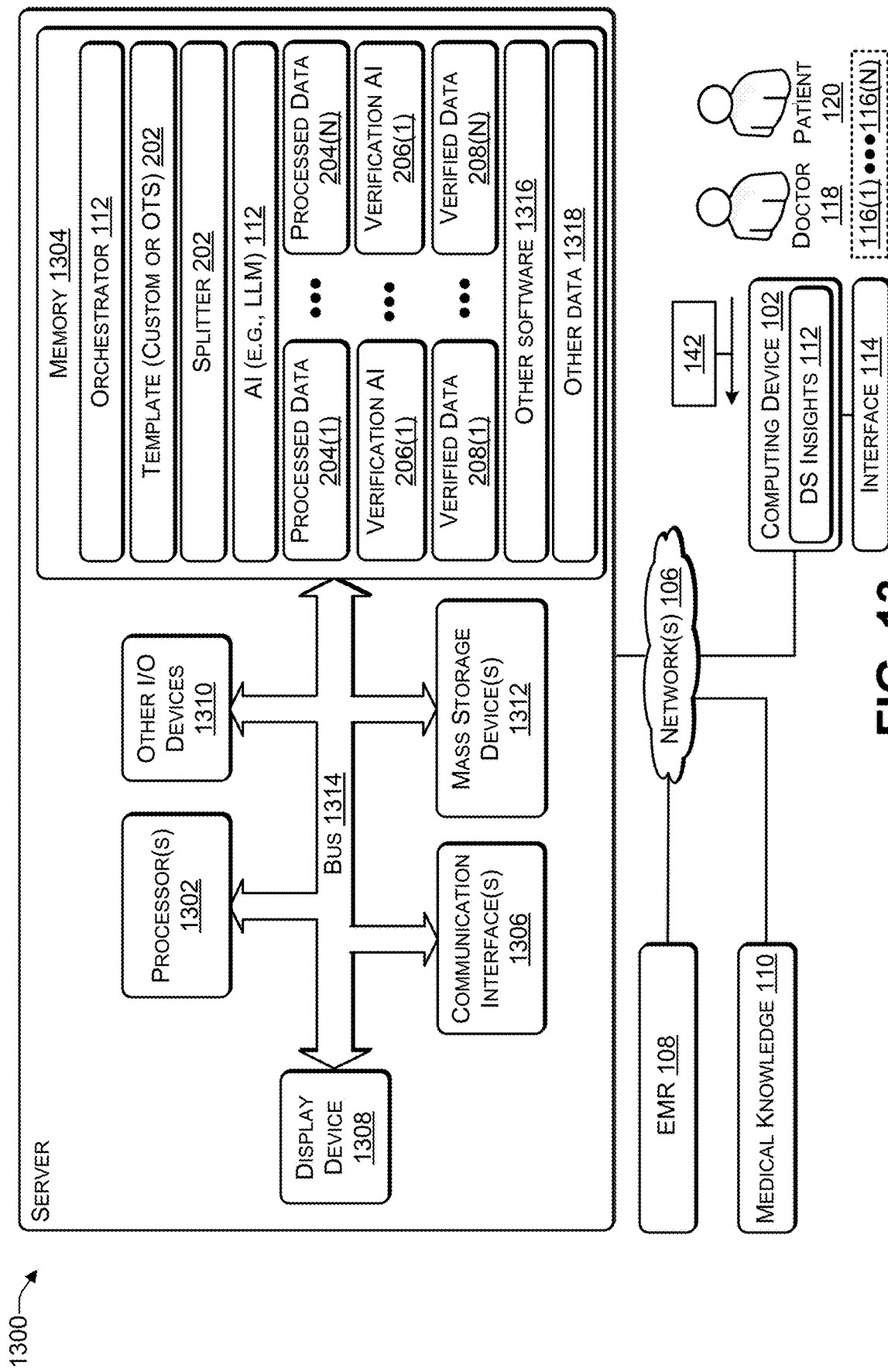
FIG. 13 illustrates an example configuration of a computing device that can be used to implement the systems and techniques described herein.

FIG. 13 illustrates an example configuration of a device 1300 that can be used to implement the systems and techniques described herein. For example, the device 1300 may be used to implement the computing device 102, the server 104, or the interface 114. For illustration purposes, FIG. 13 shows the device 1300 implementing the server 104.

The device 1300 may include one or more processors 1302 (e.g., central processing unit (CPU), graphics processing unit (GPU), or the like), a memory 1304, communication interfaces 1306, a display device 1308, other input/output (I/O) devices 1310 (e.g., keyboard, trackball, and the like), and one or more mass storage devices 1312 (e.g., disk drive, solid state disk drive, or the like), configured to communicate with each other, such as via one or more system buses 1314 or other suitable connections. While a single system bus 1314 is illustrated for ease of understanding, it should be understood that the system bus 1314 may include multiple buses, such as a memory device bus, a storage device bus (e.g., serial ATA (SATA) and the like), data buses (e.g., universal serial bus (USB) and the like), video signal buses (e.g., ThunderBolt®, digital video interface (DVI), high definition media interface (HDMI), and the like), power buses, etc.

The processors 1302 are one or more hardware devices that may include a single processing unit or a number of processing units, all of which may include single or multiple computing units or multiple cores. The processors 1302 may include a graphics processing unit (GPU) that is integrated into the CPU or the GPU may be a separate processor device from the CPU. The processors 1302 may be implemented as one or more microprocessors, microcomputers, microcontrollers, digital signal processors, central processing units, graphics processing units, state machines, logic circuitries, and/or any devices that manipulate signals based on operational instructions. Among other capabilities, the processors 1302 may be configured to fetch and execute computer-readable instructions stored in the memory 1304, mass storage devices 1312, or other computer-readable media.

Memory 1304 and mass storage devices 1312 are examples of computer storage media (e.g., memory storage devices) for storing instructions that can be executed by the processors 1302 to perform the various functions described herein. For example, memory 1304 may include both volatile memory and non-volatile memory (e.g., random access memory (RAM), read only memory (ROM), or the like) devices. Further, mass storage devices 1312 may include hard disk drives, solid-state drives, removable media, including external and removable drives, memory cards, flash memory, floppy disks, optical disks (e.g., compact disc (CD), digital versatile disc (DVD), a storage array, a network attached storage (NAS), a storage area network (SAN), or the like. Both memory 1304 and mass storage devices 1312 may be collectively referred to as memory or computer storage media herein and may be any type of non-transitory media capable of storing computer-readable, processor-executable program instructions as computer program code that can be executed by the processors 1302 as a particular machine configured for carrying out the operations and functions described in the implementations herein.

The device 1300 may include one or more communication interfaces 1306 for exchanging data via the network 106. The communication interfaces 1306 can facilitate communications within a wide variety of networks and protocol types, including wired networks (e.g., Ethernet, Data Over Cable Service Interface Specification (DOCSIS), digital subscriber line (DSL), Fiber, universal serial bus (USB) etc.) and wireless networks (e.g., wireless local area network (WLAN), global system for mobile (GSM), code division multiple access (CDMA), 802.11, Bluetooth, Wireless USB, ZigBee, cellular, satellite, etc.), the Internet and the like. Communication interfaces 1306 can also provide communication with external storage, such as a storage array, network attached storage, storage area network, cloud storage, or the like.

The display device 1308 may be used for displaying content (e.g., information and images) to users. Other I/O devices 1310 may be devices that receive various inputs from a user and provide various outputs to the user, and may include a keyboard, a touchpad, a mouse, a gaming controller (e.g., joystick, steering controller, accelerator pedal, brake pedal controller, virtual reality (VR) headset, VR glove, or the like), a printer, audio input/output devices, and so forth.

The computer storage media, such as memory 1304 and mass storage devices 1312, may be used to store any of the software and data described herein as well as other software 1316 and other data 1318.

The example systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer storage devices. Thus, the processes, components and modules described herein may be implemented by a computer program product.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

Some implementations of the technology disclosed relate to using a Transformer model to provide a multi-turn conversational system. In particular, the technology disclosed proposes a parallel input, parallel output (PIPO) multi-turn conversational system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed multi-turn conversational system is a multilayer perceptron (MLP). In another implementation, the disclosed multi-turn conversational system is a feedforward neural network. In yet another implementation, the disclosed multi-turn conversational system is a fully connected neural network. In a further implementation, the disclosed multi-turn conversational system is a fully convolution neural network. In a yet further implementation, the disclosed multi-turn conversational system is a semantic segmentation neural network. In a yet another further implementation, the disclosed multi-turn conversational system is a generative adversarial network (GAN) (e.g., CycleGAN, StyleGAN, pixelRNN, text-2-image, DiscoGAN, IsGAN). In a yet another implementation, the disclosed multi-turn conversational system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLaMA versions, BERT, SpanBERT, RoBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-ViT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, ViTB/16-FRCNN, ViT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed multi-turn conversational system is a convolution neural network (CNN) with a plurality of convolution layers. In another implementation, the disclosed multi-turn conversational system is a recurrent neural network (RNN) such as a long short-term memory network (LSTM), bi-directional LSTM (Bi-LSTM), or a gated recurrent unit (GRU). In yet another implementation, the disclosed multi-turn conversational system includes both a CNN and an RNN.

In yet other implementations, the disclosed multi-turn conversational system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed multi-turn conversational system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed multi-turn conversational system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed multi-turn conversational system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed multi-turn conversational system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed multi-turn conversational system can be an ensemble of multiple models, in some implementations.

In some implementations, the disclosed multi-turn conversational system can be trained using backpropagation-based gradient update techniques. Example gradient descent techniques that can be used for training the disclosed multi-turn conversational system include stochastic gradient descent, batch gradient descent, and mini-batch gradient descent. Some examples of gradient descent optimization algorithms that can be used to train the disclosed multi-turn conversational system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks.

What is claimed is:

1. A method, comprising:
  receiving, by one or more processors, a conversation between a doctor and a patient;
  performing, by the one or more processors, an analysis of the conversation using an artificial intelligence comprising a large language model, the artificial intelligence trained, using training data that includes multiple audio conversations between doctors and patients, to create a trained artificial intelligence;
  determining, by the one or more processors and based at least in part on the analysis, a first trigger phrase in the conversation;
  selecting, by the one or more processors, a template of a patient visit note from a plurality of templates, the template associated with the first trigger phrase, the template comprising multiple sections;
  determining, by the one or more processors and based at least in part on the analysis, a second trigger phrase in the conversation;
  selecting, by the one or more processors, a particular treatment plan from a plurality of treatment plans, the particular treatment plan associated with the second trigger phrase;
  adding, by the one or more processors, the particular treatment plan to the template;
  splitting, by the one or more processors, the conversation into multiple portions based on the template;
  adding, by the one or more processors, a first portion of the multiple portions to a first section of the template using a first instance of the trained artificial intelligence;
  adding, by the one or more processors, a second portion of the multiple portions to a second section of the template using a second instance of the trained artificial intelligence, the second portion added to the second portion in parallel with adding the first portion of to the first section;
  verifying the first section of the template, using a first verification artificial intelligence, wherein the first verification artificial intelligence is trained to verify the first section of the template;
  verifying the second section of the template, using a second verification artificial intelligence, in parallel with the first verification artificial intelligence verifying the first section, wherein the second verification artificial intelligence is trained to verify the second section of the template;
  providing, by the one or more processors, the template of the patient visit note to a device associated with the doctor; and
  re-training, by the one or more processors, the trained artificial intelligence using additional data that includes the conversation between the doctor and the patient.

2. The method of claim 1, wherein the first portion of the conversation comprises one or more of:
  a complaint associated with the patient;
  at least a portion of a history of a present illness associated with the patient;
  at least a portion of a medical history associated with the patient: or
  any combination thereof.

3. The method of claim 1, further comprising:
  adding one or more biometric measurements associated with the patient to the template, the one or more biometric measurements comprising at least one of: a body temperature, a diastolic blood pressure measurement, a systolic blood pressure measurement, a pulse rate, a blood oxygen level, an electro-cardiogram, or any combination thereof.

4. The method of claim 1, wherein the patient visit note comprises at least:
  a subjective section;
  an objective section;
  an assessment section; and
  a plan section.

5. The method of claim 4, wherein the plan section comprises at least one of:
  a physical therapy session;
  a surgery;
  dietary restrictions;
  an exercise regimen;
  one or more over-the-counter supplements;
  one or more prescription drugs;
  a referral to another doctor; or
  any combination thereof.

6. The method of claim 1, further comprising:
  generating, by the trained artificial intelligence, one or more billing codes based on the analysis of the conversation; and
  adding the one or more billing codes to the patient visit note.

7. The method of claim 1, wherein the conversation between the doctor and the patient comprises a text-based transcription created using a speech-to-text converter.

8. A server comprising:
  one or more processors; and
  one or more non-transitory computer-readable storage media to store instructions that are executable by the one or more processors to perform operations comprising:
    receiving a conversation between a doctor and a patient;
    performing, by an artificial intelligence comprising a large language model, an analysis of the conversation between the doctor and the patient, the artificial intelligence trained using training data that includes multiple audio conversations between doctors and patients to create a trained artificial intelligence;
    determining, based at least in part on the analysis, a first trigger phrase in the conversation;
    selecting a template of a patient visit note from a plurality of templates, the template associated with the first trigger phrase, the template comprising multiple sections;
    determining, based at least in part on the analysis, a second trigger phrase in the conversation;

selecting a particular treatment plan from a plurality of treatment plans, the particular treatment plan associated with the second trigger phrase;

adding the particular treatment plan to the template;

splitting the conversation into multiple portions based on the template;

adding a first portion of the multiple portions to a first section of the template using a first instance of the trained artificial intelligence;

adding a second portion of the multiple portions to a second section of the template using a second instance of the artificial intelligence, the second portion added to the second section in parallel with the first portion being added to the first section;

verifying the first section of the template, using a first verification artificial intelligence, wherein the first verification artificial intelligence is trained to verify the first section of the template;

verifying the second section of the template, using a second verification artificial intelligence, in parallel with the first verification artificial intelligence verifying the first section, wherein the second verification artificial intelligence is trained to verify the second section of the template;

providing the template of the patient visit note to a device associated with the doctor; and re-training the trained artificial intelligence using additional data that includes the conversation between the doctor and the patient.

9. The server of claim 8, further comprising:

generating, by the trained artificial intelligence, one or more billing codes based on the analysis of the conversation; and adding the one or more billing codes to the patient visit note.

10. The server of claim 8, wherein the patient visit note comprises at least:
   a subjective section;
   an objective section;
   an assessment section; and
   a plan section.

11. The server of claim 10, the plan section comprising:
   a physical therapy session;
   a surgery;
   dietary restrictions;
   an exercise regimen;
   one or more over-the-counter supplements;
   one or more prescription drugs;
   a referral to another doctor; or
   any combination thereof.

12. The server of claim 8, wherein the first portion of the conversation comprises one or more of:
   a complaint associated with the patient;
   at least a portion of a history of a present illness associated with the patient;
   at least a portion of a medical history associated with the patient or
   any combination thereof.

13. The server of claim 8, wherein the second portion of the conversation comprises a diagnosis expressed by the doctor during the conversation.

14. The server of claim 13, further comprising:

adding one or more biometric measurements associated with the patient to the template, the one or more biometric measurements comprising at least one of: a body temperature, a diastolic blood pressure measurement, a systolic blood pressure measurement, a pulse rate, a blood oxygen level, an electro-cardiogram, or any combination thereof.

15. A non-transitory computer-readable storage medium to store instructions that are executable by one or more processors to perform operations comprising:

receiving a conversation between a doctor and a patient;

performing, by an artificial intelligence comprising a large language model, an analysis of the conversation between the doctor and the patient, the artificial intelligence trained using training data that includes multiple audio conversations between doctors and patients to create a trained artificial intelligence;

determining, based at least in part on the analysis, a first trigger phrase in the conversation;

selecting a template of a patient visit note from a plurality of templates, the template associated with the first trigger phrase, the template comprising multiple sections;

determining, based at least in part on the analysis, a second trigger phrase in the conversation;

selecting a particular treatment plan from a plurality of treatment plans, the particular treatment plan associated with the second trigger phrase;

adding the particular treatment plan to the template;

splitting the conversation into multiple portions based on the template;

adding a first portion of the multiple portions to a first section of the template using a first instance of the trained artificial intelligence;

adding a second portion of the multiple portions to a second section of the template using a second instance of the artificial intelligence, the second portion added to the second section in parallel with the first portion of the conversation being added to the first section;

verifying the first section of the template, using a first verification artificial intelligence, wherein the first verification artificial intelligence is trained to verify the first section of the template;

verifying the second section of the template, using a second verification artificial intelligence, in parallel with the first verification artificial intelligence verifying the first section, wherein the second verification artificial intelligence is trained to verify the second section of the template;

providing the template of the patient visit note to a device associated with the doctor; and re-training the trained artificial intelligence using additional data that includes the conversation between the doctor and the patient.

16. The non-transitory computer-readable storage medium of claim 15, wherein the first portion of the conversation comprises one or more of:
   a complaint associated with the patient;
   at least a portion of a history of a present illness associated with the patient;
   at least a portion of a medical history associated with the patient; or
   any combination thereof.

17. The non-transitory computer-readable storage medium of claim 15, wherein the patient visit note comprises at least:
   a subjective section;
   an objective section;
   an assessment section; and
   a plan section.

18. The non-transitory computer-readable storage medium of claim 17, wherein the plan section comprises at least one of:
a physical therapy session;
a surgery;
dietary restrictions;
an exercise regimen;
one or more over-the-counter supplements;
one or more prescription drugs;
a referral to another doctor; or
any combination thereof.

19. The non-transitory computer-readable storage medium of claim 15, the operations further comprising:
generating, by the artificial intelligence, one or more billing codes based on the analysis of the conversation; and
adding the one or more billing codes to the patient visit note.

20. The non-transitory computer-readable storage medium of claim 15, further comprising:
adding one or more biometric measurements associated with the patient to the template, the one or more biometric measurements comprising at least one of: a body temperature, a diastolic blood pressure measurement, a systolic blood pressure measurement, a pulse rate, a blood oxygen level, an electro-cardiogram, or any combination thereof.

* * * * *